(12) United States Patent
Su et al.

(10) Patent No.: US 6,849,608 B2
(45) Date of Patent: Feb. 1, 2005

(54) MACROLIDE ANTIBIOTICS

(75) Inventors: Wei-Guo Su, San Diego, CA (US); Yan Chen, Guilford, CT (US)

(73) Assignee: Pfizer, Inc., New York, NY (US)

( * ) Notice: Subject to any disclaimer, the term of this patent is extended or adjusted under 35 U.S.C. 154(b) by 6 days.

(21) Appl. No.: 10/454,354

(22) Filed: Jun. 3, 2003

(65) Prior Publication Data

US 2004/0009930 A1 Jan. 15, 2004

Related U.S. Application Data

(63) Continuation of application No. 09/920,141, filed on Aug. 1, 2001, now abandoned
(60) Provisional application No. 60/223,591, filed on Aug. 7, 2000.

(51) Int. Cl.$^7$ .......................... A61K 31/70; C07H 17/08
(52) U.S. Cl. ........................ 514/29; 536/7.2; 536/7.3; 536/7.4
(58) Field of Search ................ 514/29; 536/7.2, 536/7.3, 7.4

(56) References Cited

U.S. PATENT DOCUMENTS

| | | | |
|---|---|---|---|
| 25,937 A | 2/1859 | Wu | 536/7.4 |
| 40,007 A | 4/1863 | Kaneko | 514/28 |
| 61,856 A | 5/1867 | Wu | 514/29 |
| 61,857 A | 5/1867 | Wu | 514/29 |
| 100,518 A | 5/1870 | Wu et al. | 514/29 |
| 156,027 A | 10/1874 | McMillan et al. | 514/29 |
| 3,923,784 A | 12/1975 | Kierstead et al. | 260/210 |
| 4,474,768 A | 10/1984 | Bright | 424/480 |
| 4,517,359 A | 5/1985 | Kobrehel et al. | 536/7.4 |
| 5,141,926 A * | 8/1992 | Weber et al. | 514/29 |
| 5,523,399 A | 6/1996 | Asaka et al. | 536/7.3 |
| 5,631,354 A | 5/1997 | Asaka et al. | 536/7.4 |
| 5,804,565 A | 9/1998 | Asaka et al. | 514/29 |
| 6,022,965 A | 2/2000 | Benedetti et al. | 536/125 |
| 6,025,350 A | 2/2000 | Masamune et al. | 514/183 |
| 6,096,714 A | 8/2000 | Agouridas et al. | 514/29 |
| 6,159,945 A | 12/2000 | Wu | 514/29 |
| 6,162,794 A | 12/2000 | Wu | 514/29 |
| 6,191,118 B1 | 2/2001 | Asaka et al. | 514/29 |
| 6,248,719 B1 | 6/2001 | Wu | 514/29 |
| 6,291,656 B1 | 9/2001 | Wu | 536/7.4 |
| 6,498,146 B1 * | 12/2002 | Wu | 514/29 |
| 6,518,251 B1 | 2/2003 | Cheng et al. | 514/29 |

FOREIGN PATENT DOCUMENTS

| | | | |
|---|---|---|---|
| CA | 2126665 | 7/1993 | C07H/17/08 |
| EP | 0619320 | 5/1997 | C07H/17/08 |
| EP | 1044985 | 10/2000 | C07H/17/08 |
| WO | WO 9911651 | 3/1999 | C07H/17/00 |
| WO | WO 9921869 | 5/1999 | C07H/17/08 |
| WO | WO 9921870 | 5/1999 | C07H/17/08 |
| WO | WO 9935157 | 7/1999 | C07H/17/08 |
| WO | WO 00/44761 | 8/2000 | C07H/17/00 |
| WO | WO 0110878 | 2/2001 | C07H/17/00 |
| WO | WO 0110880 | 2/2001 | C07H/17/00 |

OTHER PUBLICATIONS

Database Caplus, Chemical Abstracts Service, Columbus, OH, 1994:77599, T. Asaka, et al., "Preparation of 5–0–desosaminylerytheronolide derivatives as anitbacterial agents" XP002182602.

Database Caplus, Chemical Abstracts Service, Columbus, OH, 1999:390412, H. Kato, et al., "Preparation of erythromycin derivatives as antibacterial agents for atypical acid–fast bacterium infection" XP002182232.

\* cited by examiner

Primary Examiner—Elli Peselev
(74) Attorney, Agent, or Firm—Peter C. Richardson; Gregg C. Benson; Frank W. Forman

(57) ABSTRACT

A macrolide antibiotic of the formula

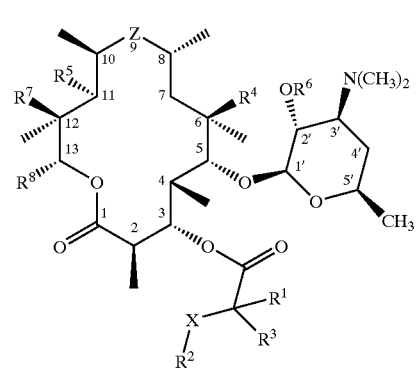

wherein the variables are defined as described herein.

6 Claims, No Drawings

MACROLIDE ANTIBIOTICS

This is a continuation application based upon and claiming priority from U.S. patent application Ser. No. 09/920,141 (abandoned), filed Aug. 1, 2001 which is based upon U.S. provisional patent application No. 60/223,591, filed Aug. 7, 2000.

BACKGROUND OF THE INVENTION

This invention relates to macrolide compounds that are useful as antibacterial and antiprotozoal agents in mammals, including man, as well as in fish and birds. This invention also relates to methods of preparing the compounds, intermediates useful in preparation of the compounds, and pharmaceutical compositions containing the compounds. In addition, the present invention includes methods of treating bacterial and protozoal infections through the administration of the compounds to mammals, fish and birds requiring such treatment.

Derivatives of erythromycin A that are useful as antibiotic agents are referred to in International patent applications WO 98/56800, published Dec. 17, 1998; WO 98/51696, published Nov. 19, 1998; WO 99/21866, published May 6, 1999; WO 99/62920, published Dec. 9, 1999; WO 99/21865, published May 6, 1999; PCT/IB99/01701, filed Oct. 18, 1999; European patent application EP 895999, published Feb. 10, 1999; U.S. patent application Ser. No. 60/117,342, filed Jan. 27, 1999; U.S. patent application Ser. No. 60/130,809, filed Apr. 23, 1999; U.S. patent application Ser. No. 60/130,912, filed Apr. 23, 1999; and U.S. patent application Ser. No. 60/130,913, filed Apr. 23, 1999. Derivatives of erythromycin A are also referred to in U.S. Pat. Nos. 4,474,768 and 4,517,359, relating to the commercially available antibiotic azithromycin. Derivatives having ester groups at the C-3 position of the macrolide ring are referred to in WO 99/21869, published May 6, 1999, and WO 98/13373, published Apr. 2, 1998. These patents and patent applications are incorporated by reference herein in their entireties.

SUMMARY OF THE INVENTION

The present invention relates to compounds of the formula

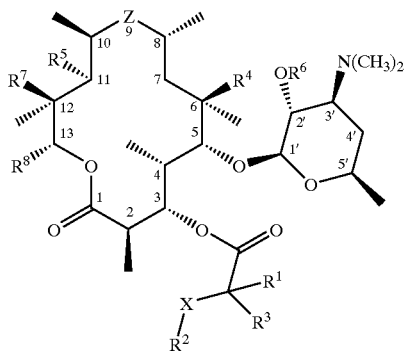

and to pharmaceutically acceptable salts, prodrugs and solvates thereof, wherein:

X is $CR^9R^{10}$, O, $NR^{11}$, or S, or X may, together with $R^2$, form a 4- to 10-membered carbocyclic or 4- to 10 membered heterocyclic group wherein said 4- to 10-membered carbocyclic or 4- to 10 membered heterocyclic group is optionally substituted by 1 to 4 $R^{14}$ groups;

Z is —C(=O)—, —C(=$NOR^{13}$)—, —CH($NR^{11}R^{12}$)—, —N($R^2$)$CH_2$—, or —$CH_2$N($R^2$)—;

$R^1$ is H, $OR^{16}$, $C_1$–$C_6$ alkyl, (4- to 10-membered heterocyclic) $C_0$–$C_6$ alkyl, or ($C_6$–$C_{10}$ aryl) $C_0$–$C_6$ alkyl;

$R^2$ is selected from H, $C_1$–$C_{16}$ alkyl, $C_2$–$C_{16}$ alkenyl, $C_2$–$C_{16}$ alkynyl, (4- to 10-membered heterocyclic) $C_0$–$C_6$ alkyl, (4- to 10-membered heterocyclic) $C_2$–$C_6$ alkenyl, (4- to 10-membered heterocyclic) $C_2$–$C_6$ alkynyl, ($C_6$–$C_{10}$ aryl) $C_0$–$C_6$ alkyl, ($C_6$–$C_{10}$ aryl) $C_2$–$C_6$ alkenyl, and ($C_6$–$C_{10}$ aryl) $C_2$–$C_6$ alkynyl, wherein the alkyl, alkenyl, and alkynyl moieties of the foregoing groups are optionally substituted by halo or $C_1$–$C_6$ alkyl, wherein one to three carbons of said $C_1$–$C_{16}$ alkyl, $C_2$–$C_{16}$ alkenyl, and $C_2$–$C_{16}$ alkynyl, are, where possible, optionally replaced by O, N or S, and further wherein the aryl and heterocyclic moieties of each of the foregoing groups and optional substituents are optionally substituted by 1 to 4 $R^{14}$ groups, or $XR^2$ may form a 4- to 10-membered carbocyclic or 4- to 10 membered heterocyclic group wherein said 4- to 10-membered carbocyclic or 4- to 10 membered heterocyclic group is optionally substituted by 1 to 4 $R^{14}$ groups;

$R^3$ is selected from $C_1$–$C_{16}$ alkyl, $C_2$–$C_{16}$ alkenyl, $C_2$–$C_{16}$ alkynyl, (4- to 10-membered heterocyclic) $C_0$–$C_6$ alkyl, (4- to 10-membered heterocyclic) $C_2$–$C_6$ alkenyl, (4- to 10-membered heterocyclic) $C_2$–$C_6$ alkynyl, ($C_6$–$C_{10}$ aryl) $C_0$–$C_6$ alkyl, ($C_6$–$C_{10}$ aryl) $C_2$–$C_6$ alkenyl, and ($C_6$–$C_{10}$ aryl) $C_2$–$C_6$ alkynyl, wherein the alkyl, alkenyl, and alkynyl moieties of the foregoing groups are optionally substituted by halo or $C_1$–$C_6$ alkyl, and further wherein the aryl and heterocyclic moieties of each of the foregoing groups and optional substituents are optionally substituted by 1 to 4 $R^{14}$ groups;

$R^1$ and $R^3$ together can form =O or =$NOR^{13}$;

$R^4$ is H or $OR^{19}$;

or Z and $R^4$ together form a group of the formula

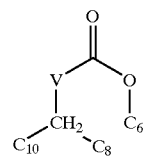

wherein $C_{10}$, $C_8$, and $C_6$ indicate carbon atoms of the macrolide ring of formula I to which the group is attached;

V is O or $NR^{17}$;

$R^5$ and $R^7$ are OH, or together form a group of the formula

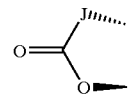

wherein J is selected from O, $NR^{15}$, $NOR^{15}$, and N—$NR^{15}$;

$R^6$ is H, —C(O)$C_1$–$C_6$ alkyl, benzyl, benzyloxycarbonyl, or ($C_1$–$C_6$ alkyl)$_3$ silyl;

$R^8$ is selected from $C_1$–$C_{10}$ alkyl, $C_2$–$C_6$ alkenyl, $C_2$–$C_6$ alkynyl, ($C_1$–$C_6$ alkoxy) $C_1$–$C_6$ alkyl, ($C_1$–$C_6$ alkylthio) $C_1$–$C_6$ alkyl, ($C_5$–$C_8$ cycloalkyl) $C_2$–$C_5$ alpha branched alkyl, $C_3$–$C_8$ cycloalkyl, $C_5$–$C_8$ cycloalkenyl, (4- to 10-membered heterocyclic) $C_1$–$C_6$ alkyl, ($C_6$–$C_{10}$ aryl) $C_1$–$C_6$ alkyl, wherein one or more carbons of $R^8$ may be replaced with one or more heteroatoms selected from O, S, N and $R^8$ is optionally substituted with from one to four $R^{14}$ groups;

$R^9$ and $R^{10}$ are independently selected from H and $C_1$–$C_6$ alkyl;

each $R^{11}$ and $R^{12}$ is independently selected from H, $C_1$–$C_6$ alkyl, $C_6$–$C_{10}$ aryl, and 4- to 10-membered heterocyclic;

each $R^{13}$ is independently selected from H, $C_1$–$C_6$ alkyl, (4- to 10-membered heterocyclic) $C_0$–$C_6$ alkyl and ($C_6$–$C_{10}$ aryl) $C_0$–$C_6$ alkyl, wherein said aryl and heterocyclic groups are optionally substituted by 1 to 4 $R^{14}$ groups;

each $R^{14}$ is independently selected from halo, cyano, nitro, trifluoromethyl, trifluoromethoxy, azido, —C(O)$R^{14a}$, —C(O)O$R^{14a}$, —OC(O)$R^{14a}$, —$NR^{11}$C(O)$R^{14a}$, —C(O)$NR^{11}R^{14a}$, —$NR^{11}R^{14a}$, hydroxy, $C_1$–$C_6$ alkyl, $C_2$–$C_6$ alkenyl, $C_2$–$C_6$ alkynyl, ($C_6$–$C_{10}$ aryl) $C_0$–$C_6$ alkyl, 4- to 10-membered heterocyclic) $C_0$–$C_6$ alkyl, $C_1$–$C_6$ alkoxy, $C_6$–$C_{10}$ aryloxy, —S(O)$_j$($C_0$–$C_6$ alkyl) wherein said $C_0$–$C_6$ alkyl is optionally substituted by 1 to 10 $R^{14a}$ groups, —S(O)$_j$($C_2$–$C_6$ alkenyl) wherein said $C_2$–$C_6$ alkenyl is optionally substituted by 1 to 7 $R^{14a}$ groups, where each j is an integer from 0 to 2, and —$SO_2NR^{11}R^{14a}$, wherein said aryl or heterocyclic group is optionally substituted by 1 to 4 $R^{14a}$ groups;

each $R^{14a}$ is independently selected from halo, cyano, nitro, trifluoromethyl, trifluoromethoxy, azido, —C(O)$R^{11}$, —C(O)O$R^{11}$, —OC(O)$R^{11}$, —$NR^{11}$C(O)$R^{12}$, —C(O)$NR^{11}R^{12}$, —$NR^{11}R^{12}$, hydroxy, $C_1$–$C_6$ alkyl, $C_2$–$C_6$ alkenyl, $C_2$–$C_6$ alkynyl, ($C_6$–$C_{10}$ aryl) $C_0$–$C_6$ alkyl, (4- to 10-membered heterocyclic) $C_0$–$C_6$ alkyl, $C_1$–$C_6$ alkoxy, $C_6$–$C_{10}$ aryloxy, —S(O)$_k$($C_0$–$C_6$ alkyl), —S(O)$_k$($C_2$–$C_6$ alkenyl) where each k is an integer from 0 to 2, and $SO_2NR^{11}R^{12}$, wherein said aryl or heterocyclic group is optionally substituted by from one to four groups selected from halo, cyano, nitro, trifluoromethyl, trifluoromethoxy, azido, —C(O)$R^{11}$, —C(O)O$R^{11}$, —OC(O)$R^{11}$, —$NR^{11}$C(O)$R^{12}$, —C(O)$NR^{11}R^{12}$, —$NR^{11}R^{12}$, hydroxy, $C_1$–$C_6$ alkyl, $C_2$–$C_6$ alkenyl, $C_2$–$C_6$ alkynyl, ($C_6$–$C_{10}$ aryl) $C_0$–$C_6$ alkyl, (4- to 10-membered heterocyclic) $C_0$–$C_6$ alkyl, $C_1$–$C_6$ alkoxy, $C_6$–$C_{10}$ aryloxy, —S(O)$_l$($C_0$–$C_6$ alkyl), —S(O)$_l$($C_2$–$C_6$ alkenyl) and —$SO_2NR^{11}R^{12}$ wherein each l is an integer from 0 to 2;

$R^{15}$ is selected from H, $C_1$–$C_{10}$ alkyl, $C_2$–$C_{10}$ alkenyl, $C_2$–$C_{10}$ alkynyl, (4- to 10-membered heterocyclic) $C_1$–$C_6$ alkyl, (4- to 10-membered heterocyclic) $C_2$–$C_6$ alkenyl, (4- to 10-membered heterocyclic) $C_2$–$C_6$ alkynyl, ($C_6$–$C_{10}$ aryl) $C_1$–$C_6$ alkyl, ($C_6$–$C_{10}$ aryl) $C_2$–$C_6$ alkenyl, and ($C_6$–$C_{10}$ aryl) $C_2$–$C_6$ alkynyl, wherein the alkyl, alkenyl, and alkynyl moieties of the foregoing groups are optionally substituted by halo or $C_1$–$C_6$ alkyl, and wherein said heterocyclic moieties are optionally substituted by (4- to 10-membered heterocyclic) $C_0$–$C_6$ alkyl, or ($C_6$–$C_{10}$ aryl) $C_0$–$C_6$ alkyl, and further wherein the aryl and heterocyclic moieties of each of the foregoing groups and optional substituents are optionally substituted by 1 to 4 $R^{14}$ groups; and $R^{16}$ is selected from H and $C_1$–$C_6$ alkyl, wherein one to three carbons of said alkyl are optionally replaced with a heteroatom selected from O, S, and N;

$R^{17}$ is H, O$R^{16}$, $NR^{16}R^{18}$, $C_1$–$C_{16}$ alkyl, ($C_6$–$C_{10}$ aryl) $C_0$–$C_6$ alkyl, or (4- to 10-membered heterocyclic) $C_0$–$C_6$ alkyl;

$R^{18}$ is H, or $C_1$–$C_6$ alkyl wherein one or more carbons of said $C_1$–$C_6$ alkyl are optionally replaced with one or more heteroatoms selected from O, N and S and optionally substituted by $R^{14}$, and $R^{19}$ is selected from H, $C_1$–$C_{16}$ alkyl, $C_2$–$C_{16}$ alkenyl, $C_2$–$C_{16}$ alkynyl, (4- to 10-membered heterocyclic) $C_0$–$C_6$ alkyl, (4- to 10-membered heterocyclic) $C_2$–$C_6$ alkenyl, (4- to 10-membered heterocyclic) $C_2$–$C_6$ alkynyl, ($C_6$–$C_{10}$ aryl) $C_0$–$C_6$ alkyl, ($C_6$–$C_{10}$ aryl) $C_2$–$C_6$ alkenyl, and ($C_6$–$C_{10}$ aryl) $C_2$–$C_6$ alkynyl, wherein the alkyl, alkenyl, and alkynyl moieties of the foregoing groups are optionally substituted by halo or $C_1$–$C_6$ alkyl, wherein one to three carbons of said $C_1$–$C_{16}$ alkyl, $C_2$–$C_{16}$ alkenyl, and $C_2$–$C_{16}$ alkynyl, are, where possible, optionally replaced by O, N or S, and further wherein the aryl and heterocyclic moieties of each of the foregoing groups and optional substituents are optionally substituted by 1 to 4 $R^{14}$ groups.

In another embodiment of the compound of the invention, the carbon to which $R^1$, $R^3$ and $XR^2$ are attached is in the R configuration.

In another embodiment of the compound of the invention, the carbon to which $R^1$, $R^3$ and $XR^2$ are attached is in the S configuration.

In another embodiment of the compound of the invention, X is O, $CR^9R^{10}$ or $NR^{11}$, $R^1$ is H, $R^2$ is H or optionally substituted $C_1$–$C_{16}$ alkyl, $C_2$–$C_6$ alkenyl, $C_1$–$C_6$ thioalkyl, ($C_6$–$C_{10}$ aryl) $C_0$–$C_6$ alkyl, or (4 to 10 membered heterocyclic) $C_0$–$C_6$ alkyl and $R^3$ is optionally substituted (4 to 10 membered heterocyclic) $C_0$–$C_6$ alkyl or optionally substituted ($C_6$–$C_{10}$ aryl) $C_0$–$C_6$ alkyl.

In another embodiment of the compound of the invention, $R^6$ is H, $R^4$ is OMe, Z is (C=O), $R^5$ and $R^7$ together with the carbons to which they are attached form $C_{11}$—NH—C(=O)—O—$C_{12}$, and $R^8$ is ethyl.

In another embodiment of the compound of the invention, $R^6$ is H, $R^4$ and Z together form a cyclic carbonate, $R^5$ and $R^7$ together form a cyclic carbonate, and $R^8$ is ethyl. In an aspect of this embodiment, X is $CR^9R^{10}$ or $NR^{11}$. In another aspect of this embodiment, $XR^2$ forms a 4- to 10-membered heterocyclic group wherein the 4- to 10-membered heterocyclic group is optionally substituted by 1 to 4 $R^{14}$ groups. In another aspect of this embodiment, $XR^2$ is optionally substituted pyrrolin-1-yl, piperidin-1-yl, morpholin-1-yl, piperazin-1-yl, or pyrrolidin-1-yl.

In another embodiment of the compound of the invention, $R^1$ is H and $R^3$ is optionally substituted 4- to 10-membered aryl or 4- to 10-membered heterocyclic.

In another embodiment of the compound of the invention, $R^3$ is optionally substituted phenyl.

In another embodiment of the compound of the invention, X is O and $R^2$ is allyl, or methoxymethyl.

In another embodiment of the compound of the invention, X is NH and $R^2$ is propyl, or optionally substituted pyrid-2-yl, pyrid-3-yl, or benzyl.

In another embodiment of the compound of the invention, $R^4$ is OH, $R^6$ is H, Z is $CHNH_2$, $R^5$ is OH, $R^7$ is OH, and $R^8$ is ethyl.

In another embodiment of the compound of the invention, $R^4$ is OH, $R^5$ is OH, $R^6$ is H, $R^7$ is OH, $R^8$ is ethyl, and Z is —N(CH$_3$)CH$_2$—.

In another embodiment of the compound of the invention, $R^4$ is OH, $R^5$ is OH, $R^6$ is H, $R^7$ is OH, $R^8$ is ethyl, and Z is —CH(NMe$_2$)—.

In another embodiment, $R^8$ is selected from methyl, n-propyl, isopropyl, cyclopropyl, propenyl, n-butyl, sec-butyl, tert-butyl, isobutyl, and cyclobutyl.

The invention also relates to a compound of the formula

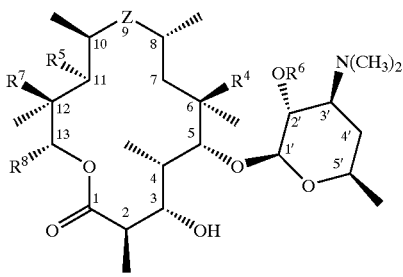

wherein:
Z is —C(=O)—, —C(=NOR$^{13}$)—, —CH(NR$^{11}$R$^{12}$)—, —N(R$^2$)CH$_2$—, or —CH$_2$N(R$^2$)—;
R$^4$ is H or OR$^{19}$;
or Z and R$^4$ together form a group of the formula

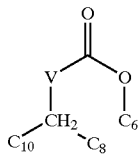

wherein C$_{10}$, C$_8$, and C$_6$ indicate carbon atoms of the macrolide ring of formula I to which the group is attached;
V is O, or NR$^{17}$;
R$^5$ and R$^7$ together form a group of the formula

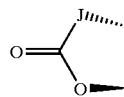

wherein J is selected from O, NR$^{15}$, NOR$^{15}$, and N—NR$^{15}$;
R$^6$ is H, —C(O)C$_1$–C$_6$ alkyl, benzyl, benzyloxycarbonyl, or (C$_1$–C$_6$ alkyl)$_3$ silyl;
R$^8$ is selected from methyl, C$_3$–C$_{10}$ alkyl, C$_2$–C$_6$ alkenyl, C$_2$–C$_6$ alkynyl, (C$_1$–C$_6$ alkoxy) C$_1$–C$_6$ alkyl, (C$_1$–C$_6$ alkylthio) C$_1$–C$_6$ alkyl, (C$_5$–C$_8$ cycloalkyl) C$_2$–C$_5$ alpha branched alkyl, C$_3$–C$_8$ cycloalkyl, C$_5$–C$_8$ cycloalkenyl, (4- to 10-membered heterocyclic) C$_1$–C$_6$ alkyl, (C$_6$–C$_{10}$ aryl) C$_1$–C$_6$ alkyl, wherein one or more carbons of R$^8$ may be replaced with one or more heteroatoms selected from O, S, N and R$^8$ is optionally substituted with from one or four R$^{14}$ groups provided that R$^8$ is not ethyl;
each R$^{11}$ and R$^{12}$ is independently selected from H, C$_1$–C$_6$ alkyl, C$_6$–C$_{10}$ aryl, and 4- to 10-membered heterocyclic;
each R$^{13}$ is independently selected from H, C$_1$–C$_6$ alkyl, (4- to 10-membered heterocyclic) C$_0$–C$_8$ alkyl and (C$_6$–C$_{10}$ aryl) C$_0$–C$_6$ alkyl, wherein said aryl and heterocyclic groups are optionally substituted by 1 to 4 R$^{14}$ groups;
each R$^{14}$ is independently selected from halo, cyano, nitro, trifluoromethyl, trifluoromethoxy, azido, —C(O)R$^{14a}$, —C(O)OR$^{14a}$, —OC(O)R$^{14a}$, —NR$^{11}$C(O)R$^{14a}$, —C(O)NR$^{11}$R$^{14a}$, —NR$^{11}$R$^{14a}$, hydroxy, C$_1$–C$_6$ alkyl, C$_2$–C$_6$ alkenyl, C$_2$–C$_6$ alkynyl, (C$_6$–C$_{10}$ aryl) C$_0$–C$_6$ alkyl, 4- to 10-membered heterocyclic) C$_0$–C$_6$ alkyl, C$_1$–C$_6$ alkoxy, C$_6$–C$_{10}$ aryloxy, —S(O)$_j$(C$_0$–C$_6$ alkyl) wherein said C$_0$–C$_6$ alkyl is optionally substituted by 1 to 10 R$^{14a}$ groups, —S(O)$_j$(C$_2$–C$_6$ alkenyl) wherein said C$_2$–C$_6$ alkenyl is optionally substituted by 1 to 7 R$^{14a}$ groups, where each j is an integer from 0 to 2, and —SO$_2$NR$^{11}$R$^{14a}$, wherein said aryl or heterocyclic group is optionally substituted by 1 to 4 R$^{14a}$ groups;

each R$^{14a}$ is independently selected from halo, cyano, nitro, trifluoromethyl, trifluoromethoxy, azido, —C(O)R$^{11}$, —C(O)OR$^{11}$, —OC(O)R$^{11}$, —NR$^{11}$C(O)R$^{12}$, —C(O)NR$^{11}$R$^{12}$, —NR$^{11}$R$^{12}$, hydroxy, C$_1$–C$_6$ alkyl, C$_2$–C$_6$ alkenyl, C$_2$–C$_6$ alkynyl, (C$_6$–C$_{10}$ aryl) C$_0$–C$_6$ alkyl, (4- to 10-membered heterocyclic) C$_0$–C$_6$ alkyl, C$_1$–C$_6$ alkoxy, C$_6$–C$_{10}$ aryloxy, —S(O)$_k$(C$_0$–C$_6$ alkyl); —S(O)$_k$(C$_2$–C$_6$ alkenyl) where each k is an integer from 0 to 2, and SO$_2$NR$^{11}$R$^{12}$, wherein said aryl or heterocyclic group is optionally substituted by from one to four groups selected from halo, cyano, nitro, trifluoromethyl, trifluoromethoxy, azido, —C(O)R$^{11}$, —C(O)OR$^{11}$, —OC(O)R$^{11}$, —NR$^{11}$C(O)R$^{12}$, —C(O)NR$^{11}$R$^{12}$, —NR$^{11}$R$^{12}$, hydroxy, C$_1$–C$_6$ alkyl, C$_2$–C$_6$ alkenyl, C$_2$–C$_6$ alkynyl, (C$_6$–C$_{10}$ aryl) C$_0$–C$_6$ alkyl, (4- to 10-membered heterocyclic) C$_0$–C$_6$ alkyl, C$_1$–C$_6$ alkoxy, C$_6$–C$_{10}$ aryloxy, —S(O)$_l$(C$_0$–C$_6$ alkyl), —S(O)$_l$(C$_2$–C$_6$ alkenyl) and —SO$_2$NR$^{11}$R$^{12}$ wherein each l is an integer from 0 to 2;
R$^{15}$ is selected from H, C$_1$–C$_{10}$ alkyl, C$_2$–C$_{10}$ alkenyl, C$_2$–C$_{10}$ alkynyl, (4- to 10-membered heterocyclic) C$_1$–C$_6$ alkyl, (4- to 10-membered heterocyclic) C$_2$–C$_6$ alkenyl, (4- to 10-membered heterocyclic) C$_2$–C$_6$ alkynyl, (C$_6$–C$_{10}$ aryl) C$_1$–C$_6$ alkyl, (C$_6$–C$_{10}$ aryl) C$_2$–C$_6$ alkenyl, and (C$_6$–C$_{10}$ aryl) C$_2$–C$_6$ alkynyl, wherein the alkyl, alkenyl, and alkynyl moieties of the foregoing groups are optionally substituted by halo or C$_1$–C$_6$ alkyl, and wherein said heterocyclic moieties are optionally substituted by (4- to 10-membered heterocyclic) C$_0$–C$_6$ alkyl, or (C$_6$–C$_{10}$ aryl) C$_0$–C$_6$ alkyl, and further wherein the aryl and heterocyclic moieties of each of the foregoing groups and optional substituents are optionally substituted by 1 to 4 R$^{14}$ groups; and
R$^{16}$ is selected from H and C$_1$–C$_6$ alkyl, wherein one to three carbons of said alkyl are optionally replaced with a heteroatom selected from O, S, and N;
R$^{17}$ is H, OR$^{16}$, NR$^{16}$R$^{18}$, C$_1$–C$_{16}$ alkyl, (C$_6$–C$_{10}$ aryl) C$_0$–C$_6$ alkyl, or (4- to 10-membered heterocyclic) C$_0$–C$_6$ alkyl;
R$^{18}$ is H, or C$_1$–C$_6$ alkyl wherein one or more carbons of said C$_1$–C$_6$ alkyl are optionally replaced with one or more heteroatoms selected from O, N and S and optionally substituted by R$^{14}$; and
R$^{19}$ is selected from H, C$_1$–C$_{16}$ alkyl, C$_2$–C$_{16}$ alkenyl, C$_2$–C$_{16}$ alkynyl, (4- to 10-membered heterocyclic) C$_0$–C$_6$ alkyl, (4- to 10-membered heterocyclic) C$_2$–C$_6$ alkenyl, (4- to 10-membered heterocyclic) C$_2$–C$_6$ alkynyl, (C$_6$–C$_{10}$ aryl) C$_0$–C$_6$ alkyl, (C$_6$–C$_{10}$ aryl) C$_2$–C$_6$ alkenyl, and (C$_6$–C$_{10}$ aryl) C$_2$–C$_6$ alkynyl, wherein the alkyl, alkenyl, and alkynyl moieties of the foregoing groups are optionally substituted by halo or C$_1$–C$_6$ alkyl, wherein one to three carbons of said C$_1$–C$_{16}$ alkyl, C$_2$–C$_{16}$ alkenyl, and C$_2$–C$_{16}$ alkynyl, are, where possible, optionally replaced by O, N, or S, and further wherein the aryl and heterocyclic moieties of each of the foregoing groups and optional substituents are optionally substituted by 1 to 4 R$^{14}$ groups.

The invention also relates to a pharmaceutical composition for the treatment of a bacterial infection or a protozoa infection in a mammal, fish, or bird which comprises a therapeutically effective amount of a compound of formula I, or a pharmaceutically acceptable salt, prodrug, or solvate thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula I or a pharmaceutically acceptable salt, prodrug, or solvate thereof.

The term "treatment", as used herein, unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G *streptococci, Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft issue infections, abscesses and osteomyelitis, and puerperal fever related to infection by *Staphylococcus aureus,* coagulase-positive *staphylococci* (i.e., *S. epidermidis, S. hemolyticus,* etc.), *Streptococcus pyogenes, Streptococcus agalactiae, Streptococcal* groups C–F (minute-colony *streptococci*), viridans *streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pailidum, Ureaplasma urealyticum,* or *Neiserra gonorrheae,* toxin diseases related to infection by *S. aureus* (food poisoning and Toxic shock syndrome), or Groups A, B, and C *streptococci*; ulcers related to infection by *Helicobacter pylori*; systemic febrile syndromes related to infection by *Borrelia recurrentis*; Lyme disease related to infection by *Bonelia burgdorferi*; conjunctivitis, keragis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by viridans *streptococci*; persistent cough related to infection by *Bordetella pertussis*; gas gangrene related to infection by *Clostridium perfringens* or *Bacteroides* spp.; and atherosclerosis related to infection by *Helicobacter pylori* or *Chiamydia pneumoniae.* Bacterial infections and protozoa infections and disorders related to such infections that may be treated or prevented in animals include the following: bovine respiratory disease related to infection by *P. haem., P. multocida, Mycoplasma bovis,* or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E. coli, Lawsonia intracellularis, Salmonella,* or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius,* coagulase neg. *Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas,* or *Prevotella*. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a method of preparing the above compound of formula I wherein $R^6$ is H, which comprises deprotecting a compound of the following formula

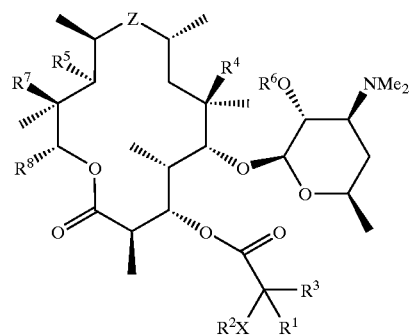

wherein $R^6$ is a protecting group.

The term "Me", as used herein, unless otherwise indicated, refers to methyl.

The term "Et", as used herein, unless otherwise indicated, refers to ethyl.

The term "Pr", as used herein, unless otherwise indicated, refers to propyl.

The term "Ac", as used herein, unless otherwise indicated, refers to acetyl.

The term "hydroxy protecting group", as used herein, unless otherwise indicated, includes acetyl, benzyloxycarbonyl, and various hydroxy protecting groups familiar to those skilled in the art including the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo.

The term "alkyl", as used herein, unless otherwise indicated, includes saturated monovalent hydrocarbon radicals having straight, cyclic or branched moieties, or mixtures thereof. It is to be understood that where cyclic moieties are intended, at least three carbons in said alkyl must be present. Such cyclic moieties include cyclopropyl, cyclobutyl and cyclopentyl.

The term "alkenyl", as used herein, unless otherwise indicated, includes straight-chain or branched-chain mono- or poly-unsaturated aliphatic hydrocarbon radicals containing at least one carbon-carbon double bond. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl", as used herein, unless otherwise indicated, includes straight-chain or branched-chain mono- or poly-unsaturated aliphatic hydrocarbon radicals containing at least one carbon-carbon triple bond. Examples of alkynyl radicals include, but are not limited to, ethynyl, propynyl, isopropynyl, butynyl, isobutynyl, pentynyl, hexynyl and the like.

The term "alkoxy", as used herein, unless otherwise indicated, includes —O-alkyl groups wherein alkyl is as defined above.

The term "aryl", as used herein, unless otherwise indicated, includes an organic radical derived from an aromatic hydrocarbon by the removal of one hydrogen. Examples of aryl radicals include, but are not limited to, phenyl, naphthyl, indenyl, indanyl, azulenyl, fluorenyl, anthracenyl and the like.

The term "4- to 10-membered heterocyclic", as used herein, unless otherwise indicated, includes aromatic and non-aromatic heterocyclic groups containing one or more heteroatoms, each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxygen or nitrogen atoms. The heterocyclic groups also include partially unsaturated or fully saturated 4- to 10-membered ring systems, e.g., single rings of 4 to 8 atoms in size and bi- or tricyclic ring systems, including aromatic 6-membered aryl or heteroaryl rings fused to a non-aromatic ring. An example of a 4-membered heterocyclic group is azetidinyl (derived from azetidine). An example of a 5-membered heterocyclic group is thiazolyl, and an example of a 10-membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.0.1.]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "protecting group" refers to a suitable chemical group that may be attached to a functional group and removed at a later stage to reveal the intact functional group. Examples of suitable protecting groups for various functional groups are described in T. W. Greene and P. G. M Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactte, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, ptoluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

The compounds of this invention, including the compounds of formula I include pharmaceutically acceptable derivatives or prodrugs thereof. A "pharmaceutically acceptable derivative or prodrug" means any pharmaceutically acceptable salt, ester, salt of an ester or other derivative of a compound of this invention that, upon administration to a recipient, is capable of providing (directly or indirectly) a compound of this invention or a metabolite or residue thereof. Particularly favored derivatives and prodrugs are those that increase the bioavailability of the compounds of this invention when such compounds are administered to a patient (e.g., by allowing an orally administered compound to be more readily absorbed into the blood), enhance delivery of the parent compound to a given biological compartment, increase solubility to allow administration by injection, after metabolism or alter rate of excretion.

Compounds of formula I can be converted into prodrugs through, for example, free amino, amido, hydroxy or carboxylic groups. Examples of such prodrugs include compounds wherein an amino acid residue, or a polypeptide chain of two or more (e.g., two, three or four) amino acid residues is covalently joined through an amide or ester bond to a free amino, hydroxy or carboxylic acid group of a compound of formula I. The amino acid residues include but are not limited to the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates and phosphoryloxymethyloxycarbonyls, as outlined in D. Fleisher et al., *Advanced Drug Delivery Reviews*, 19:115 (1996). Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Medicinal Chemistry*, 39:10 (1996).

The compounds of this invention also include pharmaceutically acceptable salts of the compounds of formula I. The term "pharmaceutically acceptable salt(s)", as used herein, unless otherwise indicated, includes salts of acidic or basic groups that may be present in the compounds of the present invention.

Compounds of the invention may exist in tautomeric form. All tautomers of the compounds of formula I are included in the invention.

DETAILED DESCRIPTION OF THE INVENTION

All patents, publications, and patent applications referred to herein are hereby incorporated by reference in their entireties.

The compounds of the present invention may be prepared according to the Schemes below. Unless otherwise indicated, the substituents of the compounds in the Schemes are defined as described above.

The starting materials used in preparing the compounds of the present invention may require proper functional group protection before various modifications can take place, and deprotection after desired modifications are complete. Hydroxyl groups are generally protected as acetates or Cbz carbonates. The relative reactivities of various hydroxyl groups in the macrolide molecules of the general type claimed in this invention have been well established. Such differences in reactivity permit selective modification of different parts of the compounds of this invention.

In the method of Scheme 1, the synthesis of compounds of the invention involves a coupling reaction of an activated carboxylic acid, such as acid chloride, acid anhydride, mixed anhydride, or acid in combination with an activating agent such as dicyclohexylcarbodiimide (DCC) or 1-[3-(dimethylamino)propyl]-3-ethylcarbodiimide hydrochloride (EDC), with an appropriately protected macrolide C-3 alcohol 3. The final compounds are prepared by acid hydrolysis of the corresponding macrolides. The preparation of macrolide C-3 alcohols is also described in WO 99/21869 and WO 98/13373.

Scheme 1

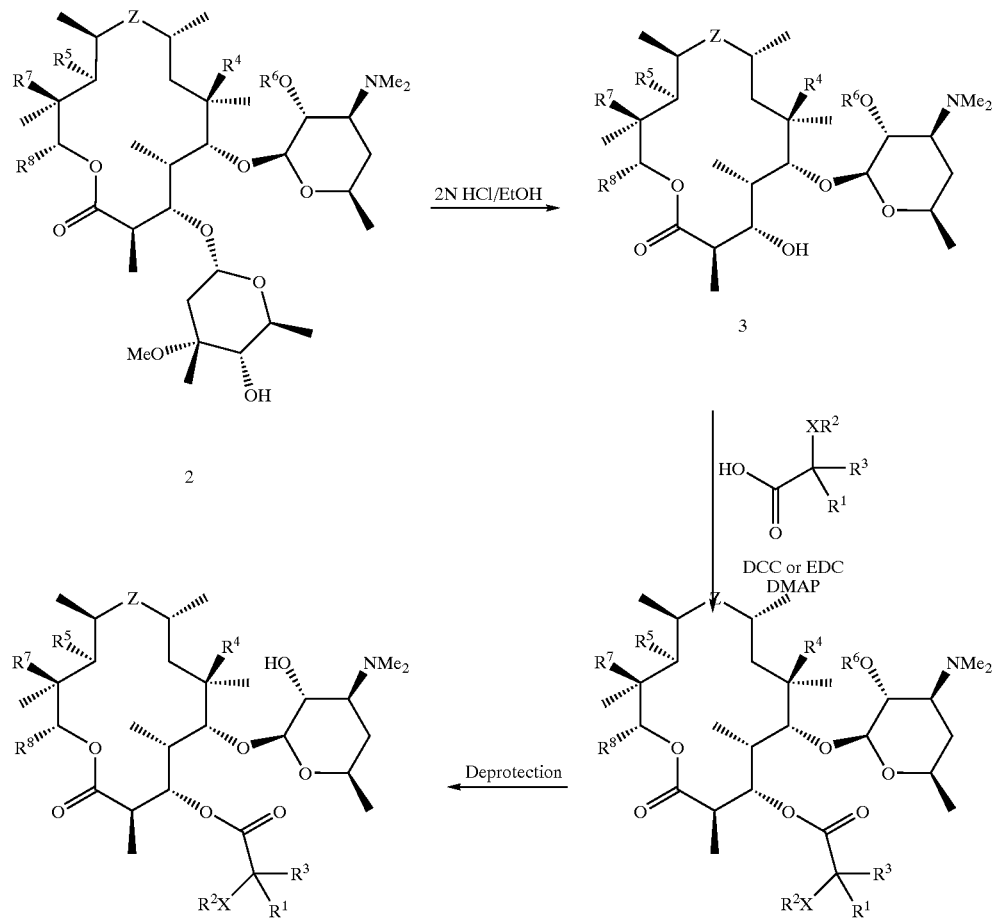

The alpha-ethers of the present invention (i.e., where X is O) are prepared by direct alkylation of the commercially available corresponding hydroxy esters, as shown in Scheme 2. Thus, racemic α-hydroxy phenylacetic acid ethyl esters are treated with an alkyl halide and a base such as sodium hydride in an aprotic solvent such as tetrahydrofuran (THF) to provide the corresponding ether. Ester hydrolysis by treatment with alkali hydroxide, such as LiOH, in tetrahydrofuran-water at 0 to 60° C. produces the corresponding carboxylic acid. Coupling of the carboxylic acid so obtained with a macrolide template 3 gives rise to the C-3 ester products 5. Deprotection affords the final products 6. The R- and S-diastereomers can be separated by silica gel chromatography (DCC, EDC, and DMAP are as defined in the Examples below).

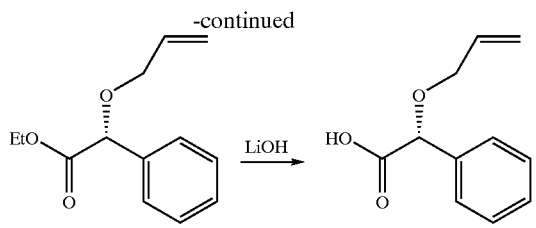

As shown in Scheme 4, the alpha amino analogues of the invention (i.e., wherein X is N) are prepared using alkyloxycarbonyl amide protected amino acids. For instance t-butyloxycarbonyl (BOC) protected phenylalanine is coupled with a macrolide template 3 to give the C-3 ester 7.

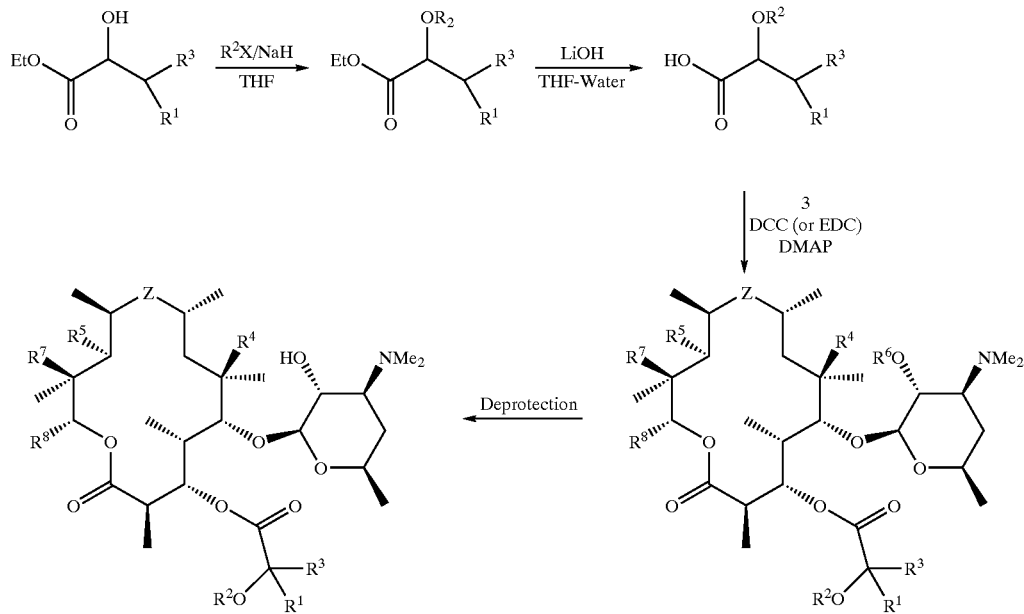

As shown in Scheme 3, allyl ethers can be obtained in optically pure form by treatment of the optically pure hydroxy esters with allyl bromide and silver oxide in a non-polar solvent such as heptane (see: G. A Krause and Y. Wu, *J. Org. Chem.*, 57, 2922 (1992)). For instance, R- or S-mandelic acid is treated with allyl bromide in the presence of silver oxide in heptane at room temperature to give the corresponding R- or S-O-allyl ether, which upon treatment with an alkali hydroxide produces the mandelic acid O-allyl ether.

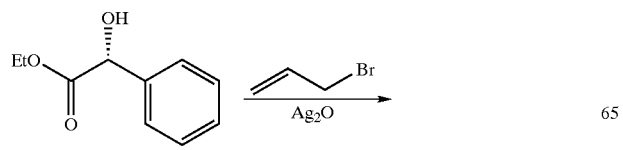

The BOC deprotection is effected by treatment with an acid, such as trifluoroacetic acid or hydrochloric acid to produce the α-amino analogue 8. Sequential reductive alkylation of the amino group provides the N-mono-alkyl 9 or N-bis-alkyl 10 derivatives.

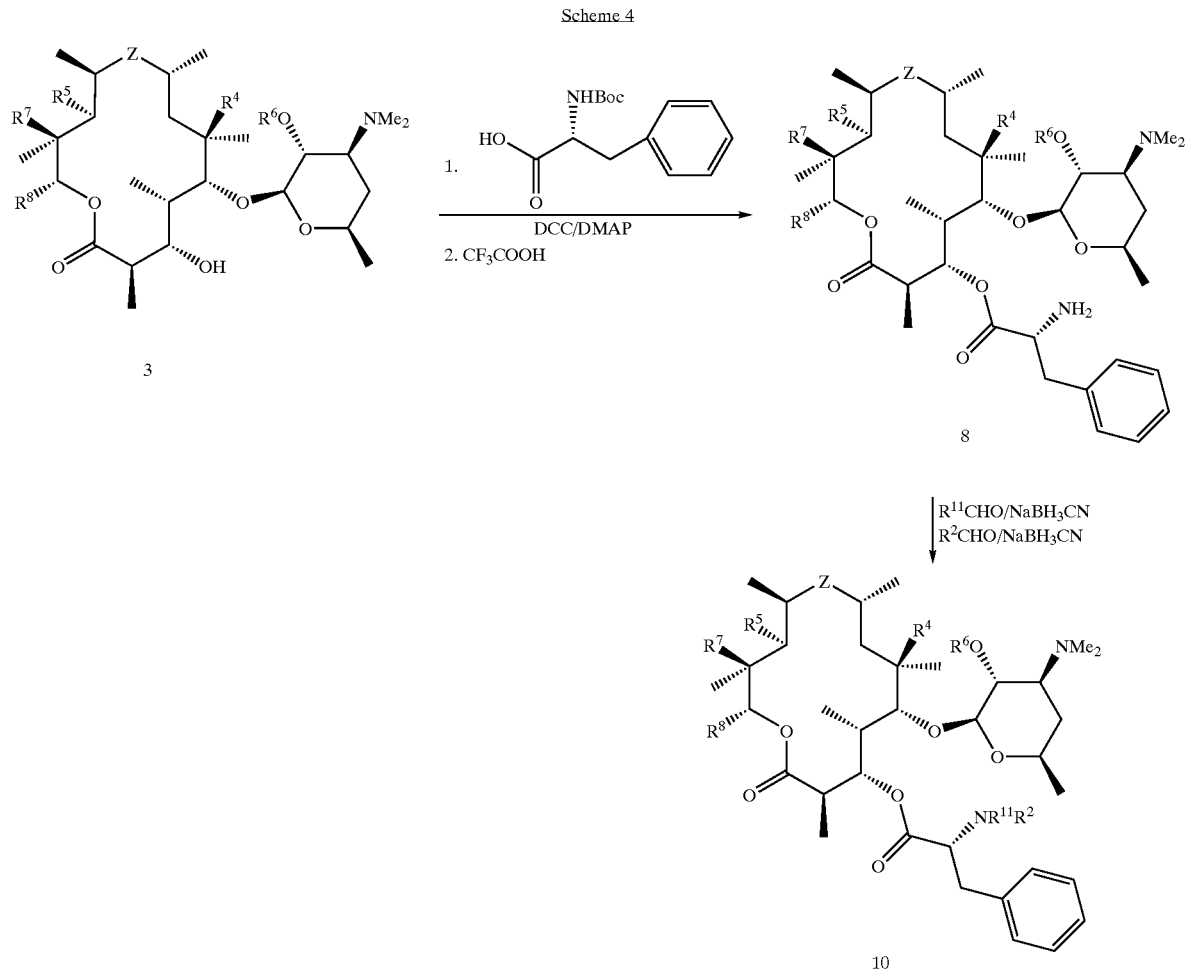

Alternatively, the alpha aminoalkyl derivatives of the invention can be prepared as illustrated below (Scheme 5).

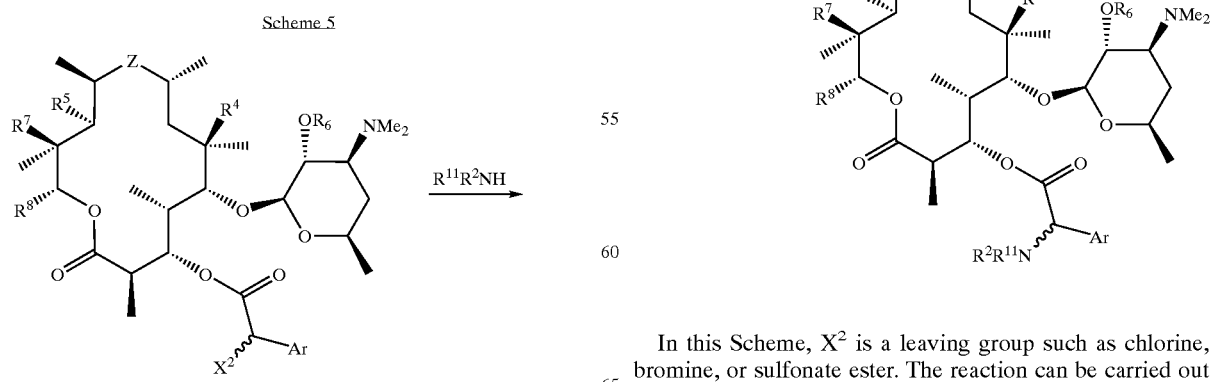

In this Scheme, $X^2$ is a leaving group such as chlorine, bromine, or sulfonate ester. The reaction can be carried out in polar organic solvents including, but not limited to, dichloromethane, dichloroethane, N,N-dimethylformamide and acetonitrile.

The alpha thioethers of the invention are prepared as depicted in Scheme 6. Thus, an alpha halo carboxylic ester is treated with a thiol in the presence of an organic or inorganic base in a variety of solvents to give the corresponding thioether (see: R. D. Schultz and F. J. McCarty, *J. Org. Chem.*, 28 (1963)). Subsequent acid hydrolysis gives the carboxylic acid, which upon coupling with a macrolide C-3 alcohol 3 provides the C-3 ester alpha thioether 11.

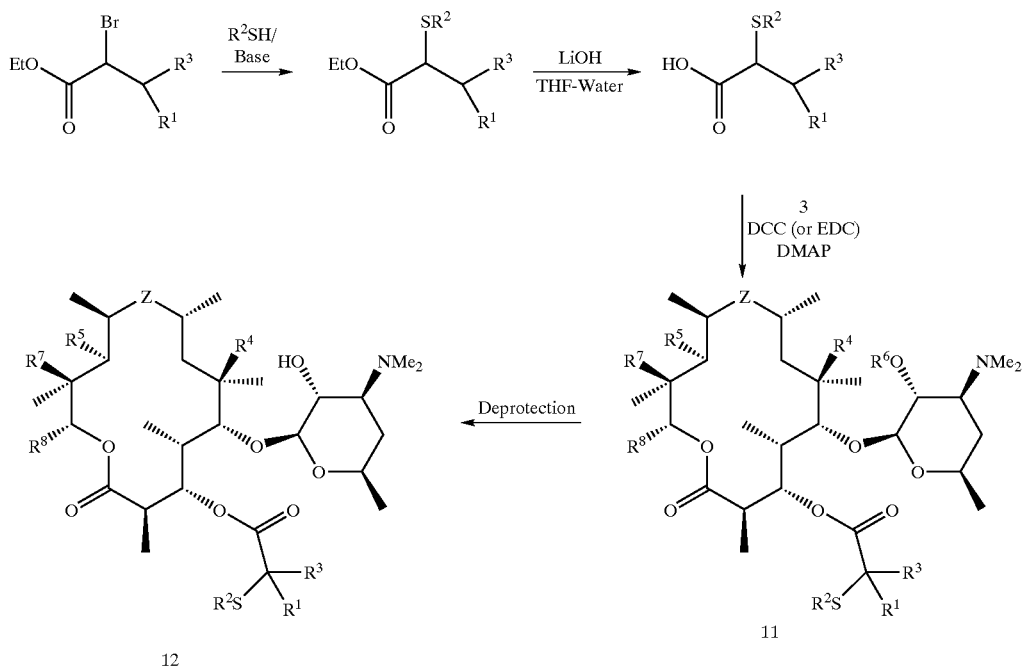

Scheme 6

The alpha carbon-linked esters of the invention are prepared following the general procedure shown in Scheme 6, starting from dialkyl malonate. Thus, sequential alkylation in the presence of a base, preferably polymer-bond base, with alkyl halides yields the alpha dialkyl-substituted malonate derivatives. Base-catalyzed acid hydrolysis followed by decarboxylation under acidic conditions produces alpha-alkyl carboxylic acids. Similarly, coupling with a macrolide template 3 gives the C-3 esters 13 and 14.

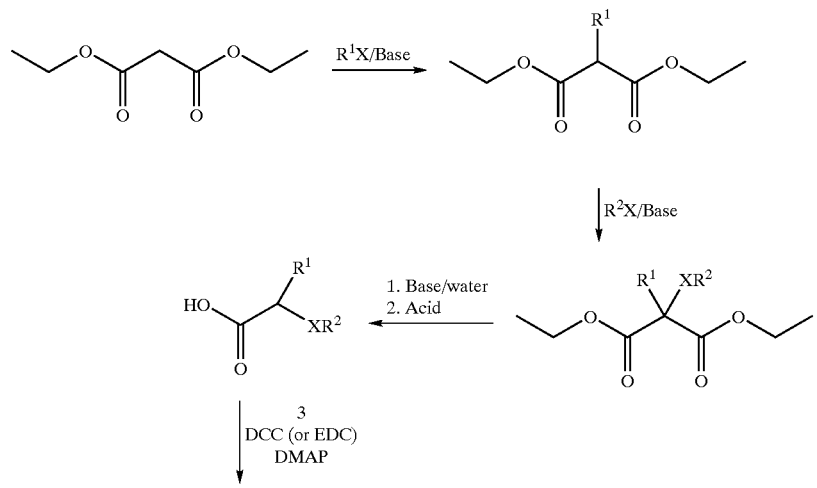

Scheme 7

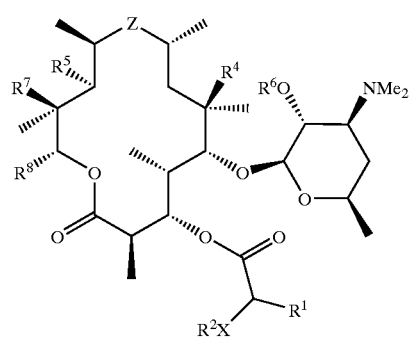

13

Deprotection →

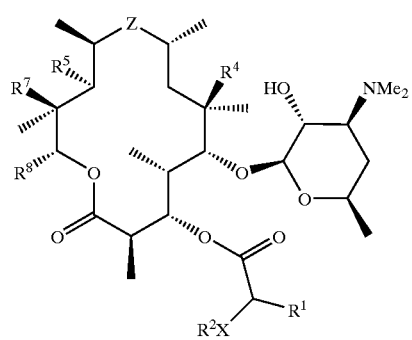

14

These alpha branched carboxylic acids can be synthesized in optically pure form by well-known procedures (see: A. G. Myers and B. H. Yang, *Org. Syn.* 77, 22 (1999)).

The alpha carbonyl derivatives of the invention 15 are prepared as illustrated in Scheme 8, where X is $C_1$–$C_4$ alkyl. Thus, treatment of a macrolide template 3 with alpha-keto-carboxylic acid chloride in the presence of a base provides the corresponding ester. Alternatively, such alpha keto esters can be obtained by oxidation of the alpha alcohol using a variety of oxidizing reagents, such as Dess-Martin reagent. These keto esters can be further transformed into the corresponding oximes or oxime ethers 18 under standard conditions (see: M. Orchiai, A. Morimoto, Y. Matsushita and T. Okada, *J. Antibiotics,* 160 (1981)).

Scheme 8

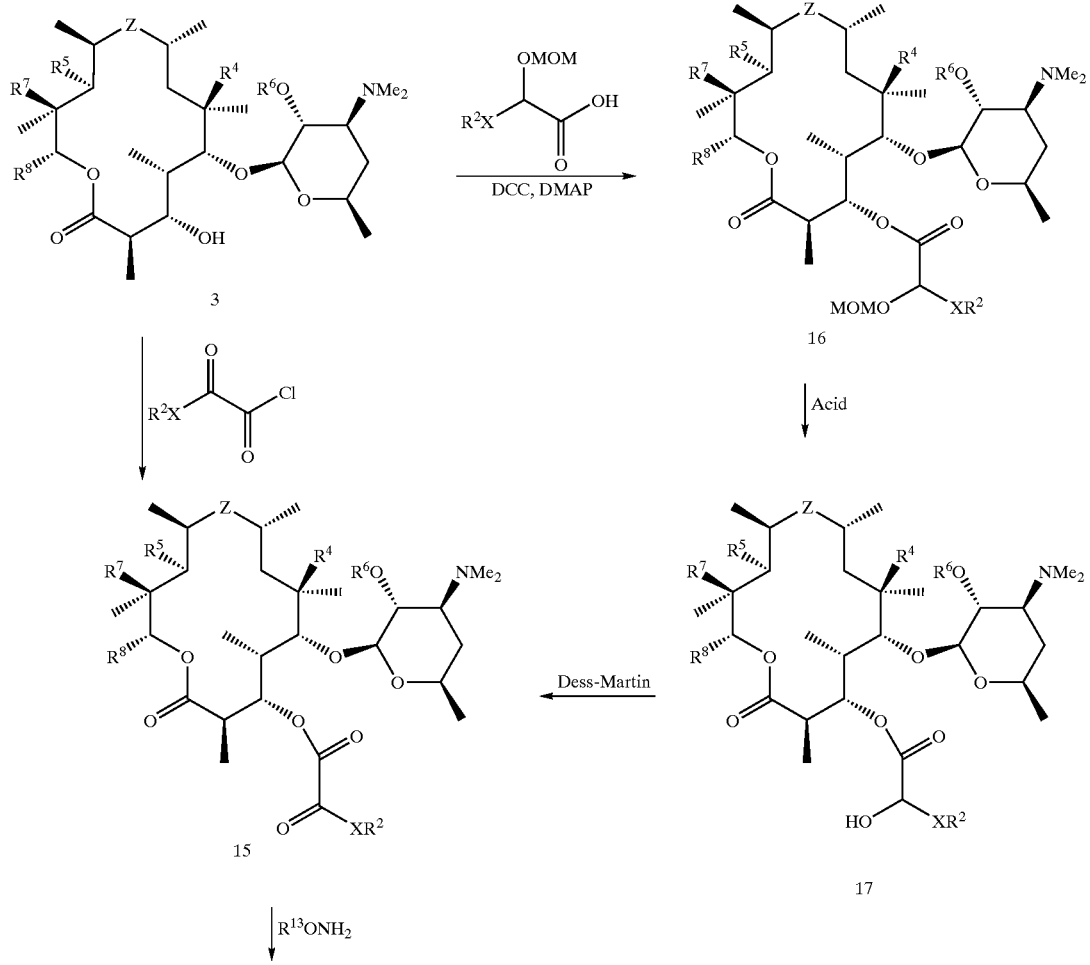

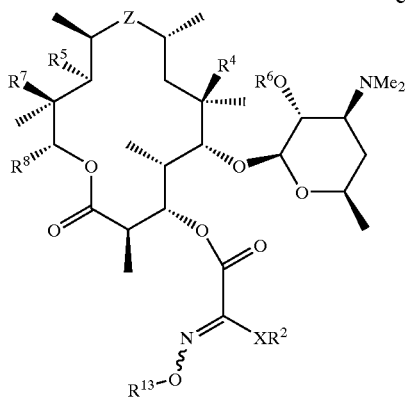

18

Compounds of the present invention wherein $R^8$ is other than ethyl may be prepared using starting materials obtained as described, e.g., in WO 98/01546, published Jan. 15, 1998; WO 98/01571, published Jan. 15, 1998; WO 00/0500, published Jan. 6, 2000; and WO 00/00618, published Jan. 6, 2000.

The compounds of the present invention may have asymmetric carbon atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The present invention includes all isotopically labelled forms of the compounds of formula I, and pharmaceutically acceptable salts and prodrugs thereof. Such isotopically labelled compounds are useful as research or diagnostic tools. The isotopically-labelled compounds and pharmaceutically acceptable salts thereof are identical to those of formula I but for the fact that one or more atoms are replaced by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Certain isotopically labelled compounds of the present invention, such as those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Substitution with heavier isotopes such as deuterium, i.e., $^2H$, can afford certain therapeutic advantages resulting from greater metabolic stability, for example, increased in vivo half-life or reduced dosage requirements, and hence may be preferred in some circumstances. Isotopically labelled compounds of formula I of this invention and prodrugs thereof can generally be prepared by carrying out the procedures disclosed in the Scheme(s) and/or in the Example(s) below and substituting a readily available isotopically labelled reagent for a non-isotopically labelled reagent.

The antibacterial and antiprotozoa activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of erm(A)/erm(B)/erm (C) are resistant to macrolides, lincosamides, and streptogramin B antibiotics due to modifications (methylation) of 23S rRNA molecules by an Erm methylase, thereby generally preventing the binding of all three structural classes. Two types of macrolide efflux have been described; msr(A) encodes a component of an efflux system in *staphylococci* that prevents the entry of macrolides and streptogramins while mef(A/E), originally described in *streptococcal* species, encodes a transmembrane protein that appears to efflux 14- and 15-membered macrolides only. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). More recently, the methodology to detect mutations in 23S rRNA of ribosomal protein L4 has been described and these mutations have been found in clinical strains of *S. pneumoniae* (A. Tait-Kamradt, et al., "Two New Mechanisms of Macrolide Resistance in Clinical Strains of *Streptococccus pneumoniae* from Eastern Europe and North America, Antimicrobial Agents and Chemotherapy, 44(12), 3395–3401 (2000). The assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare stains. Compounds are initially dissolved in dimethylsulfoxide (DMSO) as 40 mg/ml stock solutions.

| Strain Designation | Macrolide Resistance Mechanism(s) |
| --- | --- |
| Staphylococcus aureus 1116 | Macrolide susceptible |
| Staphylococcus aureus 1117 | S. aureus 1116 erm(B) |
| Staphylococcus aureus 0052 | Macrolide susceptible |
| Staphylococcus aureus 1120 | S. aureus 0052 erm(C) |
| Staphylococcus aureus 1032 | msr(A), mph, esterase |
| Staphylococcus aureus 1152 | erm(B) |
| Staphylococcus hemolyticus 1006 | msr(A), mph |
| Streptococcus pyogenes 0203 | Macrolide susceptible |
| Streptococcus pyogenes 1079 | S. pyogenes 0203 erm(B) |
| Streptococcus pyogenes 1062 | Macrolide susceptible |
| Streptococcus pyogenes 1061 | S. pyogenes 1062 erm(B) |
| Streptococcus pyogenes 1064 | mef(A) |
| Streptococcus agalactiae 1024 | Macrolide susceptible |
| Streptococcus agalactiae 1023 | S. agalactiae 1024 erm(B) |
| Streptococcus pneumoniae 1016 | Macrolide susceptible |
| Streptococcus pneumoniae 1046 | erm(B) |
| Streptococcus pneumoniae 1095 | erm(B) |
| Streptococcus pneumoniae 1229 | Low-level ketolide resistant; isogenic to strain S. pneumoniae 1095 |
| Streptococcus pneumoniae 1175 | mef(A) |
| Streptococcus pneumoniae 1231 | S. pneumoniae 1016 with 4 A2058G mutations in 23S rRNA |
| Streptococcus pneumoniae 1200 | Clinical isolate with 3 A2059G mutations in 23S rRNA |
| Streptococcus pneumoniae 1257 | Clinical strain with mutation in ribosomal protein L4 |
| Streptococcus pneumoniae 1258 | Clinical strain with mutation in ribosomal protein L4 and erm(B) that is highly ketolide resistant |
| Haemophilus influenzae 0085 | Azalide susceptible |
| Haemophilus influenzae 0131 | Azalide susceptible |
| Haemophilus influenzae 1115 | Strain Rd ΔacrB |
| Haemophllus influenzae 1116 | Strain Rd |
| Moraxella catarrhalis 0040 | Macrolide susceptible |
| Moraxella catarrhalis 1055 | Azalide susceptible; erythromycin intermediate resistance |
| Escherichia coli 0266 | Generally susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound range from 200 µg/ml to 0.098 µg/ml, achieved by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 µl of the overnight *P. haemolytica* culture is inoculated into 3 ml of fresh BHI broth and is incubated at 37° C. with shaking (200 rpm). The appropriate amounts of the test compounds are dissolved in ethanol and a series of two-fold serial dilutions are prepared, from an initial concentration of 100–200 µg/ml. Two ml of the respective serial dilution is mixed with 18 ml of molten BHI agar and solidified. When the inoculated P. haemolytica culture reaches 0.5 McFarland standard density, about 5 µl of the P. haemolytica culture is inoculated onto BHI agar plates containing the various concentrations of the test compound using a Steers Replicator and incubated for 18 hours at 37° C. The MIC is equal to the concentration of the test compound exhibiting 100% inhibition of growth of P. haemolytica as determined by comparison with an uninoculatled control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (P. multocida strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral. Subcutaneous doses are administered into the loose skin in the back of the neck whereas oral doses are given by means of a feeding needle. In both cases, compounds are delivered in a volume of 0.2 ml per mouse. Compounds are administered 30 minutes, 4 hours, and 24 hours after challenge. A control compound of known efficacy administered by the same route is included in each test. Animals are observed daily, and the number of survivors in each group is recorded. The P. multocida model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula I and the pharmaceutically acceptable salts, prodrugs, tautomers, and solvates thereof (hereinafter "the active compounds"), may be administered through oral, parenteral, topical, or rectal routes in the treatment of bacterial and protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The active compounds of the invention can also be administered in combination with other anti-infective agents, including commercially available agents such as, but not limited to, amoxicillin, penicillin, clarithromycin, cefaclor, cefuroxime, cefprozil, ciprofloxacin, clindamycin, fluconazole, dicloxacillin, erythromycin, metronidazole, ofloxacin, griseofulvin, sulfisoxazole, griseofulvin, cephalexin, terbinafine, levofloxacin, loracarbef, nitrofurantoin, minocycline, clotrimazole, nystatin, ketoconazole, cefdinir, ampicillin, trimethoprim-sulfamethoxazole, itraconazole, cefixime, mebendazole, doxycycline, sparfloxacin, and azithromycin.

The following Examples further illustrate the present invention. It is understood that the present invention is not limited to the details of the Examples.

EXAMPLE 1

Preparation of clarithromycin-11,12-carbamate-3-descladinose-3-(α-O-methoxymethyl)phenylacetic acid ester Step 1: Clarithromycin-11,12-carbamate-3-alcohol (Formula 3 wherein $R^6$ is Ac, $R^4$ is OMe, X is C=O, $R^5$ and $R^7$ together are $C_{11}$—NH—$C_{12}$—O-cyclic carbamate and $R^8$ is ethyl) (see WO 99/21869) (1 mmol) was treated with acetic anhydride (1 mmol) in anhydrous dichloromethane (10 ml) at 23° C. After 12 hours, 5% aqueous sodium carbonate was introduced and the mixture stirred for 20 minutes. The layers were separated and the aqueous phase extracted with dichloromethane (3×20 ml). Combined organic extracts were washed with brine, dried over potassium carbonate, filtered, and concentrated in vacuo to yield clarithromycin 11,12-carbamate-2'-acetyl-3-alcohol (100% yield).

Step 2: The product of Step 1 (1 mmol) was dissolved in dichloromethane (5 ml) at 0° C. and to it were added 4-dimethylaminopyridine (DMAP, 1 mmol), 1-(3[dimethylaminopropyl]-3-ethyl)-carbodiimide (EDC, 3 mmol) (or 1,3-dicyclohexylcarbodiimide (DCC, 3 mmol)) and (α-O-methoxymethyl)phenylacetic acid (3 mmol). The resulting mixture was stirred at 23° C. for 12 hours before saturated sodium bicarbonate solution was added. After stirring for 20 minutes, the layers were separated and the aqueous phase extracted with dichloromethane (3×20 ml). Combined organic extracts were washed with brine, dried over potassium carbonate, filtered, and concentrated in vacuo to afford clarithromycin 11,12-carbamate-3-descladinose-3-(α-O-methoxymethyl)phenylacetic acid ester as a mixture of R- and S-diastereomers. The two isomers were separated by silica gel column chromatography (SGC) 20% acetone-hexane as eluent. The absolute stereochemistry of the two isomers was confirmed by single crystal X-ray analysis.

Step 3: The R- and S-isomers obtained from Step 2 were separately treated with methanol at 23° C. for 24 hours. Removal of all volatiles gave the final products: clarithromycin 11,12-carbamate-3-descladinose-3-(R-O-methoxymethyl)-mandelic acid ester and clarithromycin 11,12-carbamate-3-descladinose-3-(S-O-methoxymethyl) phenylacetic acid ester.

EXAMPLE 2

Preparation of clarithromycin-11,12-carbamate-3-descladinose-3-(α-O-allyl)phenylacetic acid esters Following the procedures described in Example 1 and using (α-O-allyl)phenylacetic acid, the clarithromycin-11,12-carbamate-3-descladinose-3-(α-R-) and 3-(α-S-O-allyl)phenylacetic acid esters were prepared after SGC separation.

EXAMPLE 3

Preparation of clarithromycin-11,12-carbamate-3-descladinose-3-(α-O-methylthiomethyl)phenylacetic acid esters Following the procedures described in Example 1, and using (α-O-methylthiomethyl)phenylacetic acid, the clarithromycin-11,12-carbamate-3-descladinose-3-(α-R-) and 3-(α-S-O-methylthiomethyl)phenylacetic acid esters were prepared after SGC separation.

EXAMPLE 4

Preparation of clarithromycin-11,12-carbamate-3-descladinose-3-(α-R-amino-β-phenyl)propionic acid ester Following the procedures described in Example 1, and using α-R-t-butyloxycarbonylamido-β-phenylpropionic acid, the clarithromycin-11,12-carbamate-3-descladinose-3-(α-R-t-butyloxycarbonylamido)-β-phenylpropionic acid ester was prepared.

The product obtained above (1 mmol) was dissolved in dichloromethane (5 ml) and treated with trifluoroacetic acid (3–10 equivalents) at 23° C. for 12 hours. Water was added and the pH adjusted to 9 with 5N sodium hydroxide solution or solid sodium carbonate. Extraction with dichloromethane, drying over potassium carbonate, filtration and concentration of the filtrate to dryness afforded the title compound.

EXAMPLE 5

Preparation of clarithromycin-11,12-carbamate-3-descladinose-3-(α-S-amino-β-phenyl)propionic acid ester Following the procedures described in Example 4, and using (α-S-amino-β-phenyl)propionic acid, the title compound was prepared.

EXAMPLE 6

Preparation of clarithromycin-11,12-carbamate-3-[α-O-allyl-(p-methoxy)phenyl]acetic acid esters Following the procedures described in Example 1, and using [α-O-allyl-(p-methoxy)phenyl]acetic acid, the corresponding clarithromycin-11,12-carbamate-3-descladinose-3-(R-) and 3-(S-[α-O-allyl-(p-methoxy)phenyl]acetic acid esters were prepared after SGC separation.

EXAMPLE 7

Preparation of clarithromycin-11,12-carbamate-3-[α-O-allyl-(p-chloro)phenyl]acetic acid esters Following the procedures described in Example 1, and using [α-O-allyl-(p-chloro)phenyl]acetic acid, the corresponding clarithromycin-11,12-carbamate-3-descladinose-3-(R-) and 3-(S-[α-O-ally-(p-chloro)phenyl]acetic acid esters were prepared after SGC separation.

EXAMPLE 8

Preparation of clarithromycin-11,12-carbamate-3-[α-O-allyl-(o-methoxy)phenyl]acetic acid esters Following the procedures described in Example 1, and using [α-O-allyl-(o-methoxy)phenyl]acetic acid, the corresponding clarithromycin-11,12-carbamate-3-descladinose-3-(R-) and 3-(S-[α-O-allyl-(o-methoxy)phenyl]acetic acid esters were prepared after SGC separation.

EXAMPLE 9

Preparation of clarithromycin-11,12-carbamate-3-[α-O-allyl-(m-methoxy)phenyl]acetic acid esters Following the procedures described in Example 1, and using [α-O-allyl-(m-methoxy)phenyl]acetic acid, the corresponding clarithromycin-11,12-carbamate-3-descladinose-3-(R-) and 3-(S-[α-O-ally-(m-methoxy)phenyl]acetic acid esters were prepared after SGC separation.

EXAMPLE 10

Preparation of clarithromycin-11,12-carbamate-3-descladinose-3-(R-α-O-propyl)phenylacetic acid ester Clarithromycin-11,12-carbamate-3-descladinose-3-(R-α-O-allyl)phenylacetic acid ester (product of Example 2, 100 mg) was dissolved in methanol (5 ml) and treated with hydrogen at 40 psi in the presence of palladium on carbon (10% w/w, 10 mg) at 23° C. for 2 hours. Filtration and concentration of the filtrate produced the title compound.

EXAMPLE 11

Preparation of clarithromycin-11,12-carbamate-3-descladinose-3-(S-α-O-propyl)phenyl acetic acid ester Clarithromycin-11,12-carbamate-3-descladinose-3-(S-α-O-allyl)phenylacetic acid ester (Product of Example 2, 100 mg) was dissolved in methanol (5 ml) and treated with hydrogen at 40 psi in the presence of palladium on carbon (10% w/w, 10 mg) at 23° C. for 2 hours. Filtration and concentration of the filtrate produced the title compound.

EXAMPLE 12

Preparation of clarithromycin-11,12-carbamate-3-(α-O-benzyl)-phenylacetic acid esters Following the procedures described in Example 1, and using racemic (α-O-benzyl)-phenylacetic acid, the corresponding clarithromycin-11,12-carbamate-3-descladinose-3-(R-) and 3-(S-α-O-benzyl)-phenylacetic acid esters were prepared after SGC separation using 6% methanol-dichloromethane as eluent.

EXAMPLE 13

Preparation of erythromycin A 6,9-11,12-biscarbonate-3-descladinose-3-[R-α-(O-methoxymethyl)]phenyl acetic acid ester and related compounds Using the procedures described in Example 1, erythromycin 6,9-11,12-biscarbonate-3-alcohol (Formula 3 wherein $R^6$ is Ac, $R^4$ and Z together form a cyclic carbonate, $R^5$ and $R^7$ together form a cyclic carbonate, $R^8$ is ethyl, as described in WO 98/13373) as the macrolide template and R-α-(O-methoxymethyl)phenyl acetic acid as the carboxylic acid, the title compound was prepared in good yield as a single isomer.

By the same method, starting from 13-methyl erythromycin A 6,9-11,12-biscarbonate-3-alcohol of Formula 3 (wherein $R^6$=Ac, $R^4$ and Z taken together form a cyclic carbonate, $R^5$ and $R^7$ taken together form a cyclic carbonate, $R^8$=methyl), the compound of Formula 1, (wherein $R^4$ and Z taken together form a cyclic carbonate, $R^5$ and $R^7$ taken together form a cyclic carbonate, $R^8$=methyl, $R^1$=H, $R^2$=methoxymethyl, $R^3$=phenyl and X=O) was prepared in good yield as a single isomer.

By the same method, starting from 13-cyclobutyl erythromycin A 6,9-11,12-biscarbonate-3-alcohol of Formula 3 (wherein $R^6$=Ac, $R^4$ and Z taken together form a cyclic carbonate, $R^5$ and $R^7$ taken together form a cyclic carbonate, $R^8$=cyclobutyl), the title compound of Formula 1, (wherein $R^1$ and Z taken together form a cyclic carbonate, $R^5$ and $R^7$ taken together form a cyclic carbonate, $R^8$=cyclobutyl, $R^1$=H, $R^2$=methoxymethyl, $R^3$=phenyl and X=O) was prepared in good yield as a single isomer.

EXAMPLE 14

Preparation of erythromycin 6,9-11,12-biscarbonate-3-descladinose-3-[R-α-(O-allyl)]phenyl acetic acid ester and related compounds Using the procedures described in Example 13, and R-α-(O-allyl)-phenylacetic acid as the carboxylic acid, the title compound was prepared in good yield as a single isomer.

By the same method, starting from 13-methyl erythromycin A 6,9-11,12-biscarbonate-3-alcohol of Formula 3 (wherein $R^6$=Ac, $R^4$ and Z taken together form a cyclic carbonate, $R^5$ and $R^7$ taken together form a cyclic carbonate, $R^8$=methyl), the compound of Formula 1, (wherein $R^4$ and Z taken together form a cyclic carbonate, $R^5$ and $R^7$ taken together form a cyclic carbonate, $R^8$=methyl, $R^1$=H, $R^2$=allyl, $R^3$=phenyl and X=O) was prepared in good yield as a single isomer.

By the same method, starting from 13-cyclobutyl erythromycin A 6,9-11,12-biscarbonate-3-alcohol of Formula 3 (wherein $R^6$=Ac, $R^4$ and Z taken together form a cyclic carbonate, $R^5$ and $R^7$ taken together form a cyclic carbonate, $R^8$=cyclobutyl), the compound of Formula 1, (wherein $R^4$ and Z taken together form a cyclic carbonate, $R^5$ and $R^7$ taken together to form a cyclic carbonate, $R^8$=cyclobutyl, $R^1$=H, $R^2$=allyl, $R^3$=phenyl and X=O) was prepared in good yield as a single isomer.

EXAMPLE 15

Preparation of erythromycin 6,9-11,12-biscarbonate-3-descladinose-3-[R-α-(O-methylthiomethyl)]phenyl acetic acid ester Using the procedures described in Example 13, and R-α-(O-methylthiomethyl)phenyl acid as the carboxylic acid, the title compound was prepared in good yield as a single isomer.

EXAMPLE 16

Preparation of erythromycin 6,9-11,12-biscarbonate-3-descladinose-3-[α-O-ally-(p-methoxy)phenyl]acetic acid esters Using the procedures described in Example 13, and R/S-[α-O-allyl-(p-methoxy)phenyl]acetic acid as the carboxylic acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

EXAMPLE 17

Preparation of erythromycin 6,9-11,12-biscarbonate-3-descladinose-3-[α-O-ally-(p-chloro)phenyl]acetic acid esters Using the procedures described in Example 13, and R/S-[α-O-allyl-(p-chloro)phenyl]acetic acid as the carboxylic acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

EXAMPLE 18

Preparation of erythromycin 6,9-11,12-biscarbonate-3-descladinose-3-[α-O-allyl-(m-chloro)phenyl]acetic acid esters Using the procedures described in Example 13, and R/S-[α-O-allyl-(m-chloro)phenyl]acetic acid as the carboxylic acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

EXAMPLE 19

Preparation of erythromycin 6,9-11,12-biscarbonate-3-descladinose-3-[α-O-allyl-(o-chloro)phenyl]acetic acid esters Using the procedures described in Example 13, and R/S-[α-O-allyl-(o-chloro)phenyl]acetic acid as the carboxylic acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

EXAMPLE 20

Preparation of erythromycin 6,9-11,12-biscarbonate-3-descladinose-3-α-O-phenyl-butyric acid esters Using the procedures described in Example 13 and racemic α-O-phenyl-butyric acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

EXAMPLE 21

Preparation of erythromycin 6,9-11,12-biscarbonate-3-descladinose-3-[α-(p-methoxybenzyl)]phenylacetic acid esters and related compounds Using the procedures described in Example 13, racemic [α-(p-methoxybenzyl)]phenylacetic acid as the carboxylic acid, a mixture of R- and S-diastereomers was prepared. The pure α-R and α-S isomers of the title compound were obtained by SGC separation using 6% methanol-dichloromethane containing 0.2% concentrated ammonium hydroxide as eluent.

By the same method, substituting α-allyloxy-(2-fluoro)phenylacetic acid for α-allyloxyphenylacetic acid, the R- and S-isomers of Formula 1 (wherein $R^1$=H, $R^2$=allyl, $R^3$=(2-fluoro)phenyl, X=O, $R^4$ and Z taken together form a cyclic carbonate, $R^5$ and $R^7$ taken together form a cyclic carbonate, and $R^8$=ethyl were prepared.

By the same method, substituting α-allyloxy-(3-fluoro)phenylacetic acid for α-allyloxyphenylacetic acid, the R- and S-isomers of Formula 1 (wherein $R^1$=H, $R^2$=allyl, $R^3$=(3-fluoro)phenyl, X=O, $R^4$ and Z taken together form a cyclic carbonate, $R^5$ and $R^7$ taken together form a cyclic carbonate, and $R^8$=ethyl were prepared.

By the same method, substituting α-allyloxy-(4-fluoro)phenylacetic acid for α-allyloxyphenylacetic acid, the R- and S-isomers of Formula 1 (wherein $R^1$=H, $R^2$=allyl, $R^3$=(4-fluoro)phenyl, X=O, $R^4$ and Z taken together form a cyclic carbonate, $R^5$ and $R^7$ taken together form a cyclic carbonate, and $R^8$=ethyl were prepared.

EXAMPLE 22

Preparation of erythromycylamine 11,12-carbonate-3-descladinose-3(α-O-methoxymethyl)phenylacetic acid ester and related compounds Step 1: Erythromycylamine (Formula 2 wherein $R^4$ is OH, $R^6$ is H, Z is $CHNH_2$, $R^5$ is OH, $R^7$ is OH and $R^8$ is Et, 10 g, 13.56 mmol) was treated with N-(benzyloxycarboxy)succinimide (4.1 g, 16.27 mmol) in anhydrous dichloromethane (70 ml) at 23° C. After 18 hours, 5% aqueous sodium carbonate was introduced and the mixture stirred for 20 min. The layers were separated and the aqueous phase extracted with dichloromethane (3×50 ml). Combined organic extracts were washed with brine, dried over sodium sulfate, filtered, and concentrated in vacuo to yield N-cbz-erythromycylamine (yield: 11.81 g)

Step 2: The product of Step 1 (7.44 g) was dissolved in benzene (150 ml) and to it were added ethylene carbonate (7.44 g) and potassium carbonate (3.8 g ). The resulting mixture was heated and refluxed (bath temperature 110° C.) for 3 hours equipped with a Dean-Stock apparatus. Saturated sodium bicarbonate solution was added to the reaction mixture. After stirring for 20 minutes, the layers were separated and the aqueous phase was extracted with dichloromethane (3×20 ml). Combined organic extracts were washed with brine, dried over potassium carbonate, filtered, and concentrated in vacuo to afford 11,12-carbonate-N-cbz-erythromycylamine. The crude compound was purified by silica gel column chromatography (SGC) using 4.5% methanol-dichloromethane containing 0.45% concentrated ammonium hydroxide. (4.6 g, 60%).

Step 3: 4.6 g of 11,12-carbonate-N-cbz-erythromycylamine obtained from Step 2 was taken into 90 ml of ethanol-2 N HCl mixed solvent (1:1) and the resulting solution was stirred at room temperature for 5 hours before it was neutralized with sodium carbonate to pH 9. The excess ethanol was evaporated under vacuum and the aqueous phase was extracted with dichloromethane (3×60 ml). Combined organic extracts were washed with brine, dried over potassium carbonate, filtered, and concentrated in vacuo to afford 11,12-carbonate-3-descladinose-N-cbz-erythromycylamine. The crude compound was purified by silica gel column chromatography (SGC) using 2.0% methanol-dichloromethane containing 0.07% concentrated ammonium hydroxide. (3.14 g, 80%).

Step 4: 3.14 g of 11,12-carbonate-3-descladinose-N-cbz-erythromycylamine obtained from Step 3 was treated with 0.44 ml of acetic anhydride (1.1 eq) in 25 ml of dichloromethane at room temperature over night. The reaction mixture was taken up into 150 ml of dichloromethane and washed with saturated sodium carbonate followed by brine, dried over sodium sulfate, filtered, and concentrated in vacuo to afford 3.32 g of N-cbz-erythromycylamine-11,12-carbonate-3-descladinose-2'-acetate in quantitative yield.

Step 5: The product of Step 4 (0.5 mmol) was dissolved in dichloromethane (3 ml) at −10° C. and to it were added 4-dimethylaminopyridine (DMAP, 0.25 mmol), 1,3-dicyclohexylcarbodiimide (DCC, 1.5 mmol)) and (α-O-allyl)phenylacetic acid (1.5 mmol). The resulting mixture was allowed to warm up to room temperature and stirred at 23° C. for 1 hour. The urea was filtered off before saturated sodium bicarbonate solution was added to the reaction mixture. After stirring for 20 minutes, the layers were separated and the aqueous phase was extracted with dichloromethane (3×20 ml). Combined organic extracts were washed with brine, dried over sodium sulfate, filtered, and concentrated in vacuo to afford N-cbz-erythromycylamine-11,12-carbonate-2'-acetyl-3-descladinose-3-(α-O-allyl) phenyl acetic acid ester as a mixture of R- and S-diastereomers. The ratio of the two isomers was about 10 to 1. The compound was purified by silica gel column chromatography (SGC) using 2% methanol-dichloromethane containing 0.07% concentrated ammonium hydroxide. The yield was about 85%.

Step 6: 200 mg of the product of Step 5 was treated with 6 ml of TFA-$CH_2Cl_2$ (2:1) solution at room temperature for 2 days. Water was added and the pH adjusted to 9 with 5N sodium hydroxide solution or solid sodium carbonate. Extraction with dichloromethane, drying over potassium carbonate, filtration and concentration of the filtrate to dryness afforded erythromycylamine-11,12-carbonate-2'-acetyl-3-descladinose-3-(α-O-allyl)phenylacetic acid ester. The crude was purified by silica gel column chromatography (SGC) using 2.5% methanol-dichloromethane containing 0.08% concentrated ammonium hydroxide. The yield was about 84%.

Step 7: 90 mg of the product of Step 6 was treated with methanol at 23° C. for 48 hours. Removal of all volatiles gave the final product erythromycylamine-11,12-carbonate-3-descladinose-3-(α-O-methoxymethyl)phenylacetic acid ester in 100% yield.

By the same method, substituting 2-fluorophenylacetic acid for phenylacetic acid, the compound of Formula 1, (wherein $R^4$=OH, Z=$CHNH_2$, $R^5$ and $R^7$ taken together form a cyclic carbonate, $R^8$=methyl, $R^1$=H, $R^2$=methoxymethyl, $R^3$=2-fluorophenyl and X=O) was prepared in good yield as a single isomer.

By the same method, starting from 13-methyl erythromycylamine-3-alcohol of Formula 3 (wherein $R^6$=Ac, $R^4$=OH, Z=CHNHCbz, $R^5$ and $R^7$ taken together form a cyclic carbonate, $R^8$=methyl), the compound of Formula 1, (wherein $R^4$=OH, Z=$CHNH_2$, $R^5$ and $R^7$ taken together form a cyclic carbonate, $R^8$=methyl, $R^1$=H, $R^2$=methoxymethyl, $R^3$=phenyl and X=O) was prepared in good yield as a single isomer.

By the same method, starting from 13-cyclobutyl erythromycin A 6,9-11,12-biscarbonate-3-alcohol of Formula 3 (wherein $R^6$=Ac, $R^4$=OH, Z=CHNHCbz, $R^5$ and $R^7$ taken together form a cyclic carbonate, $R^8$=cyclobutyl), the compound of Formula 1, (wherein $R^4$=OH, Z=$CHNH_2$, $R^5$ and $R^7$ taken together to a cyclic carbonate, $R^8$=cyclobutyl, $R^1$=H, $R^2$=methoxymethyl, $R^3$=phenyl and X=O) was prepared in good yield as a single isomer.

EXAMPLE 23

Preparation of erythromycylamine-11,12-carbonate-3-descladinose-3-(R-α-O-allyl)phenylacetic acid ester and related compounds Following the procedures described in Example 22, using R-(α-O-allyl)phenylacetic acid in Step 5, the title product was obtained in good yield.

By the same method, substituting 2-fluorophenylacetic acid for phenylacetic acid, the compound of Formula 1, (wherein $R^4$=OH, Z=$CHNH_2$, $R^5$ and $R^7$ taken together form a cyclic carbonate, $R^8$=methyl, $R^1$=H, $R^2$=allyl, $R^3$=2-fluorophenyl and X=O) was prepared in good yield as a single isomer.

By the same method, starting from 13-methyl erythromycylamine-3-alcohol of Formula 3 (wherein $R^6$=Ac, $R^4$=OH, Z=CHNHCbz, $R^5$ and $R^7$ taken together form a cyclic carbonate, $R^8$=methyl), the compound of Formula 1, (wherein $R^4$=OH, Z=$CHNH_2$, $R^5$ and $R^7$ taken together form a cyclic carbonate, $R^8$=methyl, $R^1$=H, $R^2$=allyl, $R^3$=phenyl and X=O) was prepared in good yield as a single isomer.

By the same method, starting from 13-cyclobutyl erythromycin A 6,9-11,12-biscarbonate-3-alcohol of Formula 3 (wherein $R^6$=Ac, $R^4$=OH, Z=CHNHCbz, $R^5$ and $R^7$ taken together form a cyclic carbonate, $R^8$=cyclobutyl), the compound of Formula 1, ($R^4$=OH, Z=$CHNH_2$, $R^5$ and $R^7$ taken together to form a cyclic carbonate, $R^8$=cyclobutyl, $R^1$=H, $R^2$=allyl, $R^3$=phenyl and X=O) was prepared in good yield as a single isomer.

EXAMPLE 24

Preparation of erythromycylamine-11,12-carbonate-3-descladinose-3(R-) and 3-[(S)-α-O-methylthiomethyl]phenylacetic acid esters Following the procedures described in Example 22, using R/S-(α-O-methylthiomethyl)phenylacetic acids in Step 5, the title products were obtained in good yield after SGC separation using 4% methanol-dichloromethane containing 0.2% concentrated ammonium hydroxide as eluent.

EXAMPLE 25

Preparation of erythromycylamine-11,12-carbonate-3-descladinose-3-(R-) and 3-[(S)-α-O-3-(3-pyridyl)propyl]phenylacetic acid esters Following the procedures described in Example 22, using R/S-[(α-O-3-(3-pyridyl)propyl]phenylacetic acids in Step 5, the title products were obtained in good yield after SGC separation using 4% methanol-dichloromethane containing 0.2% concentrated ammonium hydroxide as eluent.

EXAMPLE 26

Preparation of erythromycylamine-11,12-carbonate-3-descladinose-3-(R-) and 3-[(S)-α-O-3-(3-pyridyl)-2-propenyl]phenylacetic acid esters Following the procedures described in Example 22, using R/S-[α-O-3-(3-pyridyl)-2-propenyl]phenylacetic acids phenylacetic acid in Step 5, the title products were obtained in good yield after SGC separation using 4% methanol-dichloromethane containing 0.2% concentrated ammonium hydroxide as eluent.

EXAMPLE 27

Preparation of erythromycylamine-11,12-carbonate-3-descladinose-3-(R-) and 3-[(S)-α-O-propyl] phenylacetic acid esters Following the procedures described in Example 10, using the products of Example 22, the title products were obtained in good yield after SGC separation using 4% methanol-dichloromethane containing 0.2% concentrated ammonium hydroxide as eluent.

EXAMPLE 28

Preparation of azithromycin-3-descladinose-3-(α-O-methoxymethyl)phenylacetic acid esters Using procedures described in Example 1 and azithromycin C-3 alcohol (Formula 3 wherein $R^6$ is Ac, $R^4$ is OH, Z is —N(CH$_3$)CH$_2$—, $R^5$ is OH, $R^7$ is OH and $R^8$ is ethyl) as starting material, azithromycin-3-descladinose-3-(R-α-O-methoxymethyl)phenylacetic acid ester and azithromycin-3-descladinose-3-(S-α-Omethoxymethyl)phenylacetic acid ester were prepared.

EXAMPLE 29

Preparation of azithromycin-11,12-carbonate-3-descladinose-3-(α-O-methoxymethyl)phenylacetic acid esters Following procedures described in Example 22, Steps 2, 3, 4, 5, and 7, using azithromycin and R-(α-O-methoxymethyl)phenylacetic acid as starting materials, the reaction produced a mixture of R- and S-diastereomers in a ratio of 2:1. The pure isomers of the title compounds were obtained after SGC separation using 4% methanol-dichloromethane containing 0.2% concentrated ammonium hydroxide as eluent.

EXAMPLE 30

Preparation of azithromycin-11,12-carbonate-3-descladinose-3-R- and S-(α-O-allyl)phenylacetic acid esters Following procedures described in Example 22, and using R-(α-O-allyl)phenylacetic acid, the reaction gave rise to a mixture of R⁻ and S⁻ diastereomers in a ratio of 2:1. The pure isomers of the title compounds were obtained after SGC separation using 4% methanol-dichloromethane containing 0.2% concentrated ammonium hydroxide.

EXAMPLE 31

Preparation of N,N-dimethylerythromycylamine-11,12-carbonate-3-descladinose-3-(α-O-methoxymethyl)phenylacetic acid esters Using procedures described in Example 22, and N,N-dimethylerythromycylamine (Formula 2 wherein $R^4$ is OH, $R^6$ is H, Z=CHNMe$_2$, $R^5$ is OH, $R^7$ is OH and $R^8$ is Et) and R-(α-O-methoxymethyl)phenylacetic acid as starting materials, the reaction generated a mixture of R- and S-diastereomers in a ratio of 3:1. The pure N,N-dimethylerythromycylamine-11,12-carbonate-3-descladinose-3-(R-) and 3-(S-α-O-methoxymethyl) phenylacetic acid esters were obtained after SGC purification.

EXAMPLE 32

Preparation of N,N-dimethylerythromycylamine-11,12-carbonate-3-descladinose-3-(α-O-allyl) phenylacetic acid esters Using procedures described in Example 22 and R-(α-O-allyl))phenylacetic acid as starting material, the reaction generated a mixture of R- and S-diastereomers in a ratio of 2:1. The pure N,N-dimethylerythromycylamine-11,12-carbonate-3-descladinose-3-(R-) and 3S-α-O-allyl) phenylacetic acid esters were obtained after SGC purification.

EXAMPLE 33

Preparation of clarithromycin 11,12-carbamate-3-descladinose-3-(α-oxo)phenylacetic acid ester Step 1: 600 mg (0.78 mmol) of the product from Step 1, Example 29 was treated with 424 mg (1.17 mmol, 1.5 eq) Dess-Martin reagent in 7 ml of dichloromethane at room temperature, stirred overnight. The resulting mixture was taken up in 100 ml of dichloromethane and washed by 5% sodium carbonate solution and brine respectively. The organic layer was separated and dried over sodium sulfate, filtered, and concentrated in vacuo to afford 2'-acetate clarithromycin 11,12-carbamate-3-descladinose-3-(α-oxo) phenylacetic acid ester. The pure compound was obtained by SGC separation using 20% acetone-hexane as eluent.

Step 2: The product obtained from Step 1 was treated with methanol at 23° C. for 24 hours. Removal of all volatiles gave the final product: clarithromycin 11,12-carbamate-3-descladinose-3-(α-oxo)phenylacetic acid ester.

EXAMPLE 34

Preparation of clarithromycin 11,12-carbamate-3-descladinose-3-(α-benzyloxime)phenylacetic acid ester 50 mg (0.06 mmol) of the product from Step 2, Example 33 was treated with benzyl hydroxyamine (10~20 eq) in 5 ml of ethanol and refluxed for 2 hours. The reaction mixture was concentrated in vacuo to afford clarithromycin 11,12-carbamate-3-descladinose-3-(α-benzyloxime)phenylacetic acid ester as a mixture of E- and Z-diastereomers. The ratio of the two isomers is about 1 to 1. The compound was purified by silica gel column chromatography (SGC) using 3% methanol-dichloromethane.

EXAMPLE 35

Preparation of clarithromycin 11,12-carbamate-3-descladinose-3-(α-methyloxime)phenylacetic acid ester 50 mg (0.06 mmol) of the product from step 2, example 33 was treated with methyl hydroxyamine (10~20 eq) in 5 ml of ethanol and refluxed for 2 hours. The reaction mixture was concentrated in vacuo to afford clarithromycin 11,12-carbamate-3-descladinose-3-(α-methyloxime)phenylacetic acid ester as a mixture of E- and Z-diastereomers. The ratio of the two isomers was about 1 to 1. The compound was purified by silica gel column chromatography (SGC) using 3.5% methanol-dichloromethane.

EXAMPLE 36

Preparation of erythromycin 6,9-11,12-biscarbonate-3-decladinose-3-(α-propylamino) phenylacetic acid ester (Formula 1 wherein Z and $R^4$ taken together form a cyclic carbonate, $R^5$ and $R^7$ taken together form a cyclic carbonate, $R^8$=ethyl, $R^1$=H, $R^2$=propyl, $R^3$=phenyl, and X=NH) and related compounds Step 1: Erythromycin 6,9-11,12-biscarbonate derivative (Formula 3 wherein Z and $R^4$ taken together form a cyclic carbonate, $R^5$ and $R^7$ taken together form a cyclic carbonate, $R^6$=Ac, $R^8$=ethyl) (672 mg, 1 mmole) was dissolved in 20 ml of dry dichloromethane and cooled to −10° C. To it were added alpha-bromophenylacetic acid (645 mg, 3 mmole), dicyclohexylcarbodiimide (618 mg, 3 mmole) and 4-dimethylaminopyridine (DMAP) (122 mg, 1 mmole). The mixture was stirred for 3 hours. The resulting suspension was filtered to remove the precipitates. The filtrate was taken up in 100 ml of ethyl acetate and successively washed with 5% $Na_2CO_3$ and brine. Drying over sodium sulfate, filtration, and evaporation of the solvent gave the crude product. The crude product was purified by SGC using acetone-hexane (1:5) as eluent to afford alpha-bromo ester in diastereomeric form.

Step 2: The product of Step 1 (100 mg) was dissolved in 1.0 ml of dry DMF under nitrogen. To it was added propylamine (3 equivalents). After stirring at room temperature for 5 hours, the reaction mixture was taken up in 30 ml of ethyl acetate, and successively washed with 30 ml of $H_2O$, 30 ml of 5% aqueous sodium carbonate and brine. Drying over sodium sulfate, filtration, evaporation of solvent and SGC purification using 5% methanol-dichloromethane containing 0.1 to 0.5% concentrated ammonium hydroxide as eluent provided the alpha-propylamino ester.

Step 3: The product of Step 2 was dissolved in methanol and the resulting solution heated at reflux for 3 hours. Removal of the solvent and purification by preparative TLC or HPLC yielded pure R- and S-(alpha-propylamino) phenylacetic acid esters (Mass Spec: 805, (M+1)).

By the same method, substituting allylamine for propylamine, the R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$=allyl, $R^3$=phenyl, and X=NH) were prepared. (Mass Spec: 803 (M+1)).

By the same method, substituting pyrid-3-ylamine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$=pyrid-3-yl, $R^3$=phenyl, and X=NH) was prepared (Mass Spec: 854 (M+1)).

By the same method, substituting pyrid-2-ylamine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$=pyrid-2-yl, $R^3$=phenyl, and X=NH) was prepared (Mass Spec: 854 (M+1)).

By the same method, substituting 2-fluorobenzylamine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$=2-fluorobenzyl, $R^3$=phenyl, and X=NH) was prepared (Mass Spec: 872 (M+1)).

By the same method, substituting 2-(2'-fluorophenyl) ethylamine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$=2-(2'-fluorophenyl)ethyl, $R^3$=phenyl, and X=NH) was prepared (Mass Spec: 885 (M+1)).

By the same method, substituting 2-(pyrid-2'-yl) ethylamine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$=2-(pyrid-2'-yl)ethyl, $R^3$=phenyl, and X=NH) were prepared (Mass Spec: 868 (M+1)).

By the same method, substituting pyrrolidine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=pyrrolin-1-yl, and $R^3$=phenyl) was prepared (Mass Spec: 817 (M+1)).

By the same method, substituting piperidine for propylamine, compound of Formula 1 (wherein Z and $R^4$ taken together form a cyclic carbonate, $R^5$ and $R^7$ taken together form a cyclic carbonate, $R^5$=ethyl, $R^1$=H, $R^2$X=piperidin-1-yl, and $R^3$=phenyl) was prepared (Mass Spec: 831 (M+1)).

By the same method, substituting morpholine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=morpholin-1-yl, and $R^3$=phenyl) was prepared (Mass Spec: 833 (M+1)).

By the same method, substituting piperazine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=piperazin-1-yl, and $R^3$=phenyl) was prepared (Mass Spec: 832 (M+1)).

By the same method, substituting 4-N-methylpiperazine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=4-N-methyl-piperazin-1-yl, and $R^3$=phenyl) was prepared (Mass Spec: 846 (M+1)).

By the same method, substituting 4-N-ethyl-piperazine for propylamine, compound of Formula 1 (wherein Z and $R^4$ taken together form a cyclic carbonate, $R^5$ and $R^7$ taken together to form a cyclic carbonate, $R^8$=ethyl, $R^1$=H, $R^2$X=4-N-ethyl-piperazin-1-yl, and $R^3$=phenyl) was prepared (Mass Spec: 860 (M+1)).

By the same method, substituting 4-benzylpiperidine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=4-benzylpiperidin-1-yl, and $R^3$=phenyl was prepared (Mass Spec: 921 (M+1)).

By the same method, substituting 4-(3-phenyl) propylpiperidine for propylamine, compound of Formula 1 (wherein Z and $R^4$ taken together form a cyclic carbonate, $R^5$ and $R^7$ taken together form a cyclic carbonate, $R^8$=ethyl, $R^1$=H, $R^2$X=4-(3-phenyl)propylpiperidin-1-yl, and $R^3$=phenyl) was prepared (Mass Spec: 949 (M+1)).

By the same method, substituting α-bromo-(2-fluorophenyl)acetic acid for α-bromo-phenylacetic acid in Step 1, the following compounds were prepared:

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$=pyrid-3-yl, $R^3$=2-fluorophenyl, and X=NH) (Mass Spec: 847 (M+1));

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$=pyrid-2-yl, $R^3$=2-fluorophenyl, and X=NH) (Mass Spec: 847 (M+1));

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$X=pyrrolidin-1-yl, and $R^3$=2-fluorophenyl) (Mass Spec: 810 (M+1));

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$X=piperidin-1-yl, and $R^3$=2-fluorophenyl) (Mass Spec: 824 (M+1));

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$X=morpholin-1-yl, and $R^3$=2-fluorophenyl) (Mass Spec: 826 (M+1));

The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$X=4-N-methylpiperazin-1-yl, and $R^3$=2-fluorophenyl) (Mass Spec: 839 (M+1)); and The R- and S-isomers of Formula 1 (wherein Z and $R^4$ taken together form a cyclic carbonate, $R^5$ and $R^7$ taken together form a cyclic carbonate, $R^8$=ethyl, $R^1$=H, $R^2$X=piperazin-1-yl, and $R^3$=2-fluorophenyl) (Mass Spec: 825 (M+1)).

EXAMPLE 37

Preparation of clarithromycin 11,12-carbamate-3-decladinose-3-(α-propylamino)phenylacetic acid ester (Formula 1 wherein Z=C=O, $R^4$=OMe, $R^5$ and $R^7$ taken together form a cyclic carbamate, $R^8$=ethyl, $R^1$=H, $R^2$=propyl, $R^3$=phenyl, and X=NH)

Following procedures of Example 36 and starting from a clarithromycin derivative (Formula 3 wherein Z=C=O, $R^4$=OMe, $R^5$ and $R^7$ taken together form a cyclic carbamate, $R^6$=Ac) gave the title compound in 20 to 50% overall yields (Mass Spec: 791 (M+1)).

EXAMPLE 38

Preparation of erythromycylamine 11,12-carbonate-3-decladinose-3-(α-propylamino)phenylacetic acid ester (Formula 1 wherein Z=CHNH$_2$, $R^4$=OH, $R^5$ and $R^7$ taken together form a cyclic carbonate, $R^8$=ethyl, $R^1$=H, $R^2$=propyl, $R^3$=phenyl, and X=NH) and related compounds Step 1: Following the procedures described in Example 36, Step 1 and starting from the erythromycylamine derivative of Formula 3 (wherein Z=CHNH$_2$, $R^4$=OH, $R^5$ and $R^7$ taken together form a cyclic carbonate, $R^6$=Ac, and $R^8$=ethyl), the corresponding alpha-bromo ester was obtained in comparable yields.

Step 2: Following the procedures of Example 36, Step 2, the corresponding alpha-propylamino ester was obtained in comparable yields.

Step 3: The product of Step 2 was dissolved in TFA-CH$_2$Cl$_2$ (2:1) solution and stirred for 5 days to remove the N-Cbz group. After aqueous work up the crude material was dissolved in methanol and refluxed for 3 hours to remove the 2'-acetate to yield the final product. The pure R- and S-isomers of the (alpha-propylamino)phenylacetic acid ester were obtained after preparative TLC or HPLC separation. Overall yields ranged between 20 to 50% (Mass Spec: 779 (M+1)).

By the same method, substituting allylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=allyl, phenyl, and X=NH) were obtained (Mass Spec: 777 (M+1)).

By the same method, substituting pyrid-3-ylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=pyrid-3-yl, $R^3$=phenyl, and X=NH) were obtained (Mass Spec: 828 (M+1)).

By the same method, substituting pyrid-2-ylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=pyrid-2-yl, $R^3$=phenyl, and X=NH) were obtained (Mass Spec: 828 (M+1)).

By the same method, substituting cyclopropylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=cyclopropyl, $R^3$=phenyl, and X=NH) were obtained (Mass Spec: 777 (M+1)).

By the same method, substituting cyclobutylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=cyclobutyl, $R^3$=phenyl, and X=NH) were obtained (Mass Spec: 791 (M+1)).

By the same method, substituting cyclopentylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=cyclopentyl, $R^3$=phenyl, and X=NH) were obtained (Mass Spec: 805 (M+1)).

By the same method, substituting cyclohexylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=cyclohexyl, $R^3$=phenyl, and X=NH) were obtained (Mass Spec: 819 (M+1)).

By the same method, substituting benzylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=benzyl, $R^3$=phenyl, and X=NH) were obtained (Mass Spec: 828 (M+1)).

By the same method, substituting 2-fluorobenzylamine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$=2-fluorobenzyl, $R^3$=phenyl, and X=NH) were obtained (Mass Spec: 846 (M+1)).

By the same method, substituting pyrrolidine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$X=pyrrolidin-1-yl, and $R^3$=phenyl) were obtained (Mass Spec. 791 (M+1)).

By the same method, substituting morpholine for propylamine, the R- and S-isomers of Formula 1 (wherein Z=CHNH$_2$, $R^4$=OH, $R^5$ and $R^7$ taken together form a cyclic carbonate, $R^8$=ethyl, $R^1$=H, $R^2$X=morpholin-1-yl, and $R^3$=phenyl) were obtained (Mass Spec: 807 (M+1)).

EXAMPLE 39

Preparation of erythromycylamine 11,12-carbonate-3-decladinose-3-(α-pyrid-3-ylamino)-(2-fluorophenyl)acetic acid ester (Formula 1 wherein Z=CHNH$_2$, $R^4$=OH, $R^5$ and $R^7$ taken together form a cyclic carbonate, $R^8$=ethyl, $R^1$=H, $R^2$=pyrid-3-yl, $R^3$=2-fluorophenyl, and X=NH)

Using the procedures described in Example 38, substituting α-bromo-2-fluorophenylacetic acid for α-bromophenylacetic acid, the compound of Formula 1 (wherein Z=CHNH$_2$, R$^4$=OH, R$^5$ and R$^7$ taken together form a cyclic carbonate, R$^8$=ethyl, R$^1$=H, R$^2$=pyrid-3-yl, R$^3$=2-fluorophenyl, and X=NH) was prepared. (Mass Spec: 846 (M+1)).

By the same method, substituting 2-(pyrid-3-yl) ethylamine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$=2-(pyrid-3-yl) ethylamine, R$^3$=2-fluorophenyl, and X=NH) was prepared. (Mass Spec: 860 (M+1)).

By the same method, substituting pyrrolidine for 3-pyridylamine, the compound of Formula 1 (Z=CHNH$_2$, R$^4$=OH, R$^5$ and R$^7$ taken together form a cyclic carbonate, R$^8$=ethyl, R$^1$=H, R$^2$X=pyrrolidin-1-yl, and R$^3$=2-fluorophenyl) was prepared. (Mass Spec: 810 (M+1)).

By the same method, substituting piperidine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$X=piperidin-1-yl, and R$^3$=2-fluorophenyl) was prepared. (Mass Spec: 824 (M+1)).

By the same method, substituting morpholine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$X=morpholin-1-yl, and R$^3$=2-fluorophenyl) was prepared. (Mass Spec: 826 (M+1)).

By the same method, substituting piperazine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$X=piperazin-1-yl, and R$^3$=2-fluorophenyl) was prepared. (Mass Spec: 815 (M+1)).

By the same method, substituting 4-N-methyl-piperazine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$X=4-N-methyl-piperazin-1-yl, and R$^3$=2-fluorophenyl) was prepared. (Mass Spec: 829 (M+1)).

By the same method, substituting 4-N-ethyl-piperazine for 3-pyridylamine, the compound of Formula 1 (wherein Z=CHNH$_2$, R$^4$=OH, R$^5$ and R$^7$ taken together form a cyclic carbonate, R$^8$=ethyl, R$^1$=H, R$^2$X=4-N-ethyl-piperazin-1-yl, and R$^3$=2-fluorophenyl) was prepared. (Mass Spec: 843 (M+1)).

What is claimed is:

1. A compound selected from the group consisting of:
   clarithromycin-11,12-carbonate-3-descladinose-3-(α-O-methoxymethyl)phenylacetic acid ester;
   clarithromycin-11,12-carbonate-3-descladinose-3-(α-O-allyl)phenylacetic acid ester,
   clarithromycin-11,12-carbonate-3-descladinose-3-(α-O-methylthiomethyl)phenylacetic acid ester,
   clarithromycin-11,12-carbonate-3-descladinose-3-(α-R-amino-β-phenyl)propionic acid ester,
   clarithromycin-11,12-carbamate-3-descladinose-3-(α-S-amino-β-phenyl)propionic acid ester,
   clarithromycin-11,12-carbamate-3-[α-O-allyl-(p-methoxy)phenylacetic acid ester;
   clarithromycin-11,12-carbamate-3-[α-O-allyl-(p-chloro) phenylacetic acid ester,
   clarithromycin-11,12-carbamate-3-[α-O-allyl-(o-methoxy)phenylacetic acid ester;
   clarithromycin-11,12-carbamate-3-[α-O-allyl-(m-methoxy)phenylacetic acid ester;
   clarithromycin-11,12-carbonate-3-descladinose-3-(R-α-O-propyl)phenylacetic acid ester;
   clarithromycin-11,12-carbonate-3-descladinose-3-(S-α-O-propyl)phenylacetic acid ester;
   erythromycin 6,9-11,12-biscarbonate-3-descladinose-3-[R-α-(O-allyl)]phenyl acetic acid ester;
   erythromycin 6,9-11,12-biscarbonate-3-descladinose-3-[R-α-(O-methylthiomethyl)phenyl]acetic acid ester;
   erythromycin 6,9-11,12-biscarbonate-3-descladinose-3-[α-O-allyl-(p-methoxy)phenyl]acetic acid ester;
   erythromycin 6,9-11,12-biscarbonate-3-descladinose-3-[α-O-allyl-(p-chloro)phenyl]acetic acid ester;
   erythromycin 6,9-11,12-biscarbonate-3-descladinose-3-[α-O-allyl-(m-chloro)phenyl]acetic acid ester,
   erythromycin 6,9-11,12-biscarbonate-3-descladinose-3-[α-O-allyl-(o-chloro)phenyl]acetic acid ester;
   erythromycin 6,9-11,12-biscarbonate-3-descladinose-3-α-O-phenyl-butyric acid ester;
   erythromycin 6,9-11,12-biscarbonate-3-descladinose-3-[α-(p-methoxybenzyl)phenylacetic acid ester;
   erythromycylamine-11,12-carbonate-3-descladinose-3-(α-O-methoxymethyl)phenylacetic acid ester;
   erythromycylamine-11,12-carbonate-3-descladinose-3-(R-α-O-allyl)phenylacetic acid ester;
   erythromycylamine-11,12-carbonate-3-descladinose-3-(R-) and 3-[(S)-α-O-methylthiomethyl]phenylacetic acid ester;
   erythromycylamine-11,12-carbonate-3-descladinose-3-(R-) and 3-[(S)-α-O-3-(3-pyridyl)propyl]phenylacetic acid ester;
   erythromycylamine-11,12-carbonate-3-descladinose-3-(R-) and 3-[(S)-α-O-3-(3-pyridyl)-2-propenyl] phenylacetic acid ester;
   erythromycylamine-11,12-carbonate-3-descladinose-3-(R-) and 3-((S)-α-O-propyl]phenylacetic acid ester;
   azithromycin-3-descladinose-3-(α-O-methoxymethyl) phenylacetic acid ester;
   azithromycin-11,12-carbonate-3-descladinose-3-(α-O-methoxymethyl)phenylacetic acid ester;
   azithromycin-11,12-carbonate-3-descladinose-3-R- and S-(α-O-alkyl)phenylacetic acid ester;
   N,N-dimethylerythromycylamine-11,12-carbonate-3-descladinose-3-(α-O-methoxymethyl)phenylacetic acid ester;
   N,N-dimethylerythromycylamine-11,12-carbonate-3-descladinose-3-(α-O-allyl)phenylacetic acid ester;
   clarithromycin 11,12-carbonate-3-descladinose-3-(α-oxo)phenylacetic acid ester;
   clarithromycin 11,12-carbonate-3-descladinose-3-(α-benzyloxime)phenylacetic acid ester;
   clarithromycin 11,12-carbonate-3-descladinose-3-(α-methyloxime)phenylacetic acid ester; and
   the foregoing compounds wherein the C13 substituent is selected from methyl, n-propyl, isopropyl, cyclopropyl, propenyl, n-butyl, sec-butyl, isobutyl, and cyclobutyl; or
   a pharmaceutically acceptable salt, prodrug, or solvate thereof.

2. A compound of the formula which is selected from the group consisting of compounds wherein:
$R^6$=H, $R^4$ and Z taken together form a cyclic carbonate, $R^5$ and $R^7$ taken together form a cyclic carbonate, $R^8$=methyl, $R^1$=H, $R^2$=methoxymethyl, $R^3$=phenyl, and X=O;
$R^6$=H, $R^4$ and Z taken together form a cyclic carbonate, $R^5$ and $R^7$ taken together form a cyclic carbonate, $R^8$=cyclobutyl, $R^1$=H, $R^2$=methoxymethyl, $R^3$=phenyl, and X=O;
$R^6$=H, $R^4$ and Z taken together form a cyclic carbonate, $R^5$ and $R^7$ taken together form a cyclic carbonate, $R^8$=methyl, $R^1$=H, $R^2$=allyl, $R^3$=phenyl, and X=O;
$R^6$=H, $R^4$ and Z taken together form a cyclic carbonate, $R^5$ and $R^7$ taken together to form a cyclic carbonate, $R^8$=cyclobutyl, $R^1$=H, $R^2$=allyl, $R^3$=phenyl, and X=O;
$R^6$=H, $R^1$=H, $R^2$=allyl, $R^3$=(2-fluoro)phenyl, X=O, $R^4$ and Z taken together form a cyclic carbonate, $R^5$ and $R^7$ taken together form a cyclic carbonate, and $R^8$=ethyl;
$R^6$=H, $R^1$=H, $R^2$=allyl, $R^3$=(3-fluoro)phenyl, X=O, $R^4$ and Z taken together form a cyclic carbonate, $R^5$ and $R^7$ taken together form a cyclic carbonate, and $R^8$=ethyl;
$R^5$=H, $R^1$=H, $R^2$=allyl, $R^3$=(4-fluoro)phenyl, X=O, $R^4$ and Z taken together form a cyclic carbonate, $R^5$ and $R^7$ taken together form a cyclic carbonate, and $R^8$=ethyl;
$R^6$=H, $R^4$=OH, Z=CHNH$_2$, $R^5$ and $R^7$ taken together form a cyclic carbonate, $R^8$=methyl, $R^1$=H, $R^2$=methoxymethyl, $R^3$=2-fluorophenyl, and X=O;
$R^6$=H, $R^4$=OH, Z=CHNH$_2$, $R^5$ and $R^7$ taken together form a cyclic carbonate, $R^8$=methyl, $R^1$=H, $R^2$=methoxymethyl, $R^3$=phenyl, and X=O;
$R^6$=H, $R^4$=OH, Z=CHNH$_2$, $R^5$ and $R^7$ taken together to a cyclic carbonate, $R^8$=cyclobutyl, $R^1$=H, $R^2$=methoxymethyl, $R^3$=phenyl, and X=O;
$R^6$=H, $R^4$=OH, Z=CHNH$_2$, $R^5$ and $R^7$ taken together form a cyclic carbonate, $R^8$=methyl, $R^1$=H, $R^2$=allyl, $R^3$=2-fluorophenyl, and X=O;
$R^6$=H, $R^4$=OH, Z=CHNH$_2$, $R^5$ and $R^7$ taken together farm a cyclic carbonate, $R^8$=methyl, $R^1$=H, $R^2$=allyl, $R^3$=phenyl, and X=O;
$R^6$=H, $R^4$=OH, Z=CHNH$_2$, $R^5$ and $R^7$ taken together to form a cyclic carbonate, $R^8$=cyclobutyl, $R^1$=H, $R^2$=allyl, $R^3$=phenyl and X=O;
$R^6$=H, Z and $R^4$ taken together form a cyclic carbonate, $R^5$ and $R^7$ taken together form a cyclic carbonate, $R^8$=ethyl, $R^1$=H, $R^2$=propyl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=allyl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=pyrid-3-yl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=pyrid-2-yl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=2-fluorobenzyl; $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=2-(2'-fluorophenyl)ethyl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=2-(pyrid-2'-yl)ethyl, $R^3$=phenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$X=pyrrolin-1-yl, and $R^3$=phenyl;
$R^6$=H, Z and $R^4$ taken together form a cyclic carbonate, $R^5$ and $R^7$ taken together form a cyclic carbonate, $R^8$=ethyl, $R^1$=H, $R^2$X=piperidin-1-yl, and $R^3$=phenyl;
$R^6$=H, Z and $R^4$ taken together form a cyclic carbonate, $R^5$ and $R^7$ taken together form a cyclic carbonate; $R^5$=ethyl, $R^1$=H, $R^2$X=morpholin-1-yl, and $R^3$=phenyl;
$R^6$=H, Z and $R^4$ taken together form a cyclic carbonate, $R^5$ and $R^7$ taken together form a cyclic carbonate, $R^8$=ethyl, $R^1$=H, $R^2$X=piperazin-1-yl, and $R^3$=phenyl;
$R^6$=H, Z and $R^4$ taken together form a cyclic carbonate, $R^5$ and $R^7$ taken together form a cyclic carbonate, $R^3$=ethyl, $R^1$=H, $R^2$X=4-N-methyl-piperazin-1-yl, and $R^3$=phenyl;
$R^6$=H, Z and $R^4$ taken together form a cyclic carbonate, $R^5$ and $R^7$ taken together to form a cyclic carbonate, $R^8$=ethyl, $R^1$=H, $R^2$X=4-N-ethyl-piperazin-1-yl, and $R^3$=phenyl;
$R^6$=H, Z and $R^4$ taken together form a cyclic carbonate, $R^5$ and $R^7$ taken together form a cyclic carbonate, $R^8$=ethyl, $R^1$=H, $R^2$X=4-benzylpiperidin-1-yl, and $R^3$=phenyl;
$R^6$=H, Z and $R^4$ taken together form a cyclic carbonate, $R^5$ and $R^7$ taken together form a cyclic carbonate, $R^8$=ethyl, $R^1$=H, $R^2$X=4-(3=phenyl) propylpiperidin-1-yl, and $R^3$=phenyl;
$R^6$=H, Z and $R^4$ taken together form a cyclic carbonate, $R^5$ and $R^7$ taken together form a cyclic carbonate, $R^8$=ethyl, $R^1$=H, $R^2$=pyrid-3-yl, $R^3$=2-fluorophenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$=pyrid-2-yl, $R^3$=2-fluorophenyl, and X=NH;
$R^6$=H, Z and $R^4$ taken together form a cyclic carbonate, $R^5$ and $R^7$ taken together form a cyclic carbonate, $R^8$=ethyl, $R^1$=H, $R^2$X=pyrrolidin-1-yl, and $R^3$=2-fluorophenyl;
$R^6$=H; Z and $R^4$ taken together form a cyclic carbonate, $R^5$ and $R^7$ taken together form a cyclic carbonate, $R^8$=ethyl, $R^1$=H, $R^2$X=piperidin-1-yl, and $R^3$=2-fluorophenyl;

$R^6$=H, Z and $R^4$ taken together form a cyclic carbonate, $R^5$ and $R^7$ taken together form a cyclic carbonate, $R^8$=ethyl, $R^1$=H, $R^2X$=morpholin-1-yl, and $R^3$=2-fluorophenyl;

$R^6$=H, Z and $R^4$ taken together form a cyclic carbonate, $R^5$ and $R^7$ taken together form a cyclic carbonate, $R^8$=ethyl, $R^1$=H, $R^2X$=4-N-methylpiperazin-1-yl, and $R^3$=2-fluorophenyl;

$R^6$=H, Z and $R^4$ taken together form a cyclic carbonate, $R^5$ and $R^7$ taken together form a cyclic carbonate, $R^8$=ethyl, $R^1$=H, $R^2X$=piperazin-1-yl, and $R^3$=2-fluorophenyl;

$R^6$=H, Z=C=O, $R^4$=OMe, $R^5$ and $R^7$ taken together form a cyclic carbonate, $R^8$=ethyl, $R^1$=H, $R^2$=propyl, $R^3$=phenyl, and X=NH;

$R^6$=H, Z=CHNHZ, $R^4$=OH, Ra and $R^7$ taken together form a cyclic carbonate, $R^8$=ethyl, $R^1$=H, $R^2$=propyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=allyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=pyrid-3-yl, $R^3$=phenyl, and X=NH;

$R^6$=H, Z=CHNH$_2$, $R^4$=OH, $R^5$ and $R^7$ taken together form a cyclic carbonate, $R^6$ ethyl, $R^1$=H, $R^2$=pyrid-2-yl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=cyclopropyl, $R^3$=phenyl, and X=NH;

$R^6$=H, Z=CHNH$_2$, $R^4$=OH, $R^5$ and $R^7$ taken together form a cyclic carbonate, $R^8$ ethyl, $R^1$=H, $R^2$=cyclobutyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=cyclopentyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=cyclohexyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2$=benzyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^{20=2}$-fluorobenzyl, $R^3$=phenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2X$=pyrrolidin-1-yl, and $R^3$=phenyl;

$R^6$=H, Z=CHNH$_2$, $R^4$=OH, $R^5$ and $R^7$ taken together form a cyclic carbonate, $R^8$=ethyl, $R^1$=H, $R^2X$=morpholin-1-yl, and $R^3$=phenyl;

$R^6$=H, Z=CHNH$_2$, $R^4$=OH, $R^5$ and $R^7$ taken together form a cyclic carbonate, $R^8$=ethyl, $R^1$=H, $R^2$=pyrid-3-yl, $R^3$=2-fluorophenyl, and X=NH;

$R^6$=H; Z=CHNH$_2$, $R^4$=OH, $R^5$ and $R^7$ taken together form a cyclic carbonate, $R^8$=ethyl, $R^1$=H, $R^2$=2-(pyrid-3-yl)ethylamine, $R^3$=2-fluorophenyl, and X=NH;

$R^6$=H, Z=CHNH$_2$, $R^4$=OH, $R^5$ and $R^7$ taken together form a cyclic carbonate, $R^8$=ethyl, $R^1$=H, $R^2X$=pyrrolidin-1-yl, and $R^3$=2-fluorophenyl;

$R^6$=H, Z=CHNH$_2$, $R^4$=OH, $R^5$ and $R^7$ taken together form a cyclic carbonate, $R^8$=ethyl, $R^1$=H, $R^2X$=piperazin-1-yl, and $R^3$=2-fluorophenyl;

$R^6$=H, Z=CHNH$_2$, $R^4$=OH, $R^5$ and $R^7$ taken together form a cyclic carbonate, $R^8$=ethyl, $R^1$=H, $R^2X$=morpholin-1-yl, and $R^3$=2-fluorophenyl;

$R^6$=H, Z=CHNH$_2$, $R^4$=OH, $R^5$ and $R^7$ taken together form a cyclic carbonate, $R^8$=ethyl, $R^1$=H, $R^2X$=piperazin-1-yl, and $R^3$=2-fluorophenyl;

$R^6$=H, Z=CHNH$_2$, $R^4$=OH, $R^5$ and $R^7$ taken together form a cyclic carbonate, $R^8$=ethyl, $R^1$=H, $R^2X$=4-N-methyl-piperazin-1-yl, and $R^3$=2-fluorophenyl; and $R^6$=H, Z=CHNH$_2$, $R^4$=OH, $R^5$ and $R^7$ taken together form a cyclic carbonate, $R^8$=ethyl, $R^1$=H, $R^2X$=4-N-ethyl-piperazin-1-yl, and $R^3$=2-fluorophenyl; or a pharmaceutically acceptable salt, prodrug, or solvate thereof.

3. A pharmaceutical composition for the treatment of a bacterial infection or a protozoa infection in a mammal, fish, or bird which comprises a therapeutically effective amount of a compound of claim 1 or a pharmaceutically acceptable salt, prodrug, or solvate thereof, and a pharmaceutically acceptable carrier.

4. A pharmaceutical composition for the treatment of a bacterial infection or a protozoa infection in a mammal, fish, or bird which comprises a therapeutically effective amount of a compound of claim 2 or a pharmaceutically acceptable salt, prodrug, or solvate thereof, and a pharmaceutically acceptable carrier.

5. A method of treating a bacterial infection or a protozoa infection in a mammal, fish, or bird which comprises administering to said mammal, fish or bird a therapeutically effective amount of a compound of claim 1 or a pharmaceutically acceptable salt, prodrug, or solvate thereof.

6. A method of treating a bacterial infection or a protozoa infection in a mammal, fish, or bird which comprises administering to said mammal, fish or bird a therapeutically effective amount of a compound of claim 2 or a pharmaceutically acceptable salt, prod rug, or solvate thereof.

* * * * *